US009603876B2

(12) United States Patent
Blaser et al.

(10) Patent No.: US 9,603,876 B2
(45) Date of Patent: Mar. 28, 2017

(54) COMPOSITIONS AND METHODS FOR RESTORING GASTROINTESTINAL MICROBIOTA FOLLOWING ANTIBIOTIC TREATMENT

(75) Inventors: Martin J. Blaser, New York, NY (US); Ilseung Cho, New York, NY (US); Laura M. Cox, Morgan Hill, CA (US)

(73) Assignee: New York University, New York, NY (US)

( * ) Notice: Subject to any disclaimer, the term of this patent is extended or adjusted under 35 U.S.C. 154(b) by 572 days.

(21) Appl. No.: 12/566,965

(22) Filed: Sep. 25, 2009

(65) Prior Publication Data

US 2010/0074872 A1    Mar. 25, 2010

Related U.S. Application Data

(60) Provisional application No. 61/100,172, filed on Sep. 25, 2008, provisional application No. 61/181,970, filed on May 28, 2009.

(51) Int. Cl.
*A61K 35/74* (2015.01)
*A61K 35/741* (2015.01)

(52) U.S. Cl.
CPC ............ *A61K 35/74* (2013.01); *A61K 35/741* (2013.01)

(58) Field of Classification Search
None
See application file for complete search history.

(56) References Cited

U.S. PATENT DOCUMENTS

| | | |
|---|---|---|
| 6,348,452 B1 | 2/2002 | Brown et al. |
| 2001/0001711 A1 | 5/2001 | Olshenitsky et al. |
| 2002/0048567 A1 | 4/2002 | Olshenitsky et al. |
| 2002/0048568 A1 | 4/2002 | Olshenitsky et al. |
| 2002/0048569 A1 | 4/2002 | Olshenitsky et al. |
| 2002/0048570 A1 | 4/2002 | Olshenitsky et al. |
| 2002/0051772 A1 | 5/2002 | Olshenitsky et al. |
| 2002/0051773 A1 | 5/2002 | Olshenitsky et al. |
| 2002/0051774 A1 | 5/2002 | Olshenitsky et al. |
| 2002/0051775 A1 | 5/2002 | Olshenitsky et al. |
| 2002/0051776 A1 | 5/2002 | Olshenitsky et al. |
| 2002/0054866 A1 | 5/2002 | Olshenitsky et al. |
| 2002/0054867 A1 | 5/2002 | Olshenitsky et al. |
| 2002/0054868 A1 | 5/2002 | Olshenitsky et al. |
| 2002/0071835 A1 | 6/2002 | Olshenitsky et al. |
| 2004/0028689 A1 | 2/2004 | Borody |
| 2004/0052909 A1 | 3/2004 | Contento et al. |
| 2004/0265291 A1 | 12/2004 | Drake et al. |
| 2005/0037089 A1 | 2/2005 | Jobbins |
| 2005/0176001 A1 | 8/2005 | Nakano et al. |
| 2006/0088514 A1 | 4/2006 | O'Mahony et al. |
| 2007/0009577 A1 | 1/2007 | Mankowitz |
| 2008/0131401 A1 | 6/2008 | Brown et al. |
| 2009/0035329 A1 | 2/2009 | Blaser et al. |
| 2009/0324736 A1 | 12/2009 | Johnson et al. |
| 2010/0172874 A1 | 7/2010 | Turnbaugh et al. |
| 2011/0280840 A1 | 11/2011 | Blaser et al. |
| 2012/0058094 A1 | 3/2012 | Blaser et al. |
| 2012/0171193 A1 | 7/2012 | Blaser et al. |
| 2012/0276149 A1 | 11/2012 | Littman et al. |

FOREIGN PATENT DOCUMENTS

| | | |
|---|---|---|
| EP | 1886680 | 2/2008 |
| WO | 97/34591 | 9/1997 |
| WO | 00/75284 A1 | 12/2000 |
| WO | 01/15715 A2 | 3/2001 |
| WO | 2009/018447 A2 | 2/2009 |
| WO | WO 2012/024638 | 2/2012 |
| WO | 2013/037068 A1 | 3/2013 |
| WO | 2013/050792 A1 | 4/2013 |

OTHER PUBLICATIONS

Hopkins et al., Gut. Feb. 2001; 48(2): 198-205.*
Zoetendal et al., Gut 2008;57;1605-1615.*
Bartosch et al., Applied and Environmental Microbiology, Jun. 2004, vol. 70, No. 6, p. 3575-3581.*
Sonnenburg et al., PLoS Biol, vol. 4(12): e413, pp. 2213-2226.*
Andersson et al., PLoS ONE, Jul. 1, 2008, vol. 3, Issue 7, e2836, pp. 1-8.*
Sonnerburg et al. PLoS Biol, vol. 4(12): e413, pp. 2213-2226 (2006).*
Ley et al., (2006) Nature, 444:1022-1023.*
DiBaise et al. (Mayo Clinic Proceedings, Apr. 2008, vol. 83(4), pp. 460-469).*
Holzapfel et al., "Overview of gut flora and probiotics," Int J Food Microbiol 41:85-101, 1998.
Tuohy et al, "Using probiotics and prebiotics to improve gut health," Therapeutic Focus 8(15):692-700, 2003.
Hong Hye Jin et al, "Differential suppression of allergen-induced airway inflammation in murine model of asthma by lactic acid bacteria", FASEB Journal, vol. 22, 2008, abstract.
Stockert K, "Physiological intestinal flora in children of 6 to 12 years of age with bronchial asthma", Deutsche Zeitschrift Fur Akupunktur 2001 DE, vol. 44, No. 4, 2001, pp. 268-271 (English abstract provided).
Morris et al, "Helicobacter pylori infection link to lower rates of asthma", Lancet Infectious Diseases, Elsevier Ltd., US, vol. 7, No. 6, 2007, p. 379.
Extended European Search Report, dated Feb. 28, 2013, which issued during the prosecution of European Patent Application No. 09816896.6.
Cho, et al., Antibiotics in early life alter the murine colonic microbiome and adiposity, Nature 488(7413): 621-626. (2012).

(Continued)

*Primary Examiner* — Irene Marx
(74) *Attorney, Agent, or Firm* — Troutman Sanders LLP

(57) ABSTRACT

The present invention relates to characterizing changes in mammalian bacterial gastrointestinal, cutaneous and nasal microbiota associated with antibiotic treatment and various disease conditions (such as asthma, allergy, obesity, metabolic syndrome, gastrointestinal reflux disease (GERD), eosinophilic esophagitis, gastro-esophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, etc.) and related diagnostic and therapeutic methods. Therapeutic methods of the invention involve the use of live bacterial inoculants that are capable of restoring healthy mammalian bacterial gastrointestinal, skin, and nasal microbiota.

13 Claims, 20 Drawing Sheets

(56) References Cited

OTHER PUBLICATIONS

Cox, et al., Altering the Intestinal Microbiota during a Critical Developmental Window Has Lasting Metabolic Consequences, Cell 158: 705-721. (2014).
Trasande, et al., Infant antibiotic exposures and early-life body mass, Int J Obes (Lond) 37(1): 16-23. (2013).
Ajslev, et al., Childhood overweight after establishment of the gut microbiota: the role of delivery mode, pre-pregnancy weight and early administration of antibiotics, International Journal of Obesity 35: 522-529. (2011).
Azad, et al., Infant antibiotic exposure and the development of childhood overweight and central adiposity, International Journal of Obesity 38: 1290-1298, (2014).
Mueller, et al., Prenatal exposure to antibiotics, cesarean section and risk of childhood obesity, Int J Obes (Lond) 39(4): 665-670. (2015).
Bailey, et al., Association of Antibiotics in Infancy With Early Childhood Obesity, JAMA Pediatr. 168(11):1063-1069. (2014).
Jess, T., Microbiota, Antibiotics, and Obesity, N. Engl. J. Med. 371(26): 2526-2528. (2014).
Cox, L, and Blaser, M., Pathways in Microbe-Induced Obesity, Cell Metab. 17(6): 883-894. (2013).
Cox, L., and Blaser, M., Antibiotics in early life and obesity, Nat. Rev. Endocrinol. 11: 182-190. (2015).
Hill, et al., The International Scientific Association for Probiotics and Prebiotics consensus statement on the scope and appropriate use of the term probiotic, Nat. Rev. Gastroenterol. Hepatol. 11: 506-514. (2014).
Parks et al., Genetic Control of Obesity and Gut Microbiota Composition in Response to High-Fat, High-Sucrose Diet in Mice, Cell Metabolism 17: 141-152. (2013).
Armougom et al., Monitoring Bacterial Community of Human Gut Microbiota Reveals an Increase in Lactobacillus in Obese Patients and Methanogens in Anorexic Patients, PLoS ONE, vol. 4, p. e7125, 2009.
Armougom et al., Use of pyrosequencing and DNA barcodes to monitor variations in Firmicutes and Bacteroidetes communities in the gut microbiota of obese humans, BMC Genomics, vol. 9, p. 576, 2008.
Blaser et al., Does Helicobacter pylori protect against asthma and allergy? Gut, vol. 57, pp. 561-567, 2008.
Chen et al., *Helicobacter pylori* Colonization is Inversely Associated with Childhood Asthma, Journal of Infectious Diseases, vol. 198, pp. 553-560, 2008.
Cho et al., Antibiotics in early life alter the murine colonic microbiome and adiposity, Nature, vol. 488, pp. 621-626, 2012.
Duncan et al., Cultivable bacterial diversity from the human colon, Letters in Applied Microbiology, vol. 44, pp. 343-350, 2007.
Eckburg et al., Diversity of the Human Intestinal Microbial Flora, Science, vol. 308, pp. 1635-1638, 2005.
Flint, Antibiotics and adiposity, Nature, vol. 488, pp. 601-602, 2012.
Flint, The significance of prokaryote diversity in the human gastrointestinal tract, in SGM symposium 66: Prokaryotic Diversity: mechanisms and significance, Logan et al., eds., Cambridge University Press, pp. 65-90, 2012.
Fuller, Probiotics in man and animals, J. Applied Bacteriol., vol. 66, pp. 365-378, 1989.
Gao et al., Molecular analysis of human forearm superficial skin bacterial biota, Proc. Natl. Acad. Sci. USA, vol. 104, pp. 2927-2932, 2007.
Gao et al., Substantial Alterations of the Cutaneous Bacterial Biota in Psoriatic Lesions, PLoS One, vol. 3, pp. e2719-2728, 2008.
International Preliminary Report on Patentability issued in International Appl. No. PCT/US2009/058351, dated Mar. 29, 2011.
International Search Report issued in International Appl. No. PCT/US2009/058351, dated May 10, 2010.
International Search Report issued in International Appl. No. PCT/US2011/048501, dated Mar. 13, 2012.
Ley et al., Obesity alters gut microbial ecology, Proc. Natl. Acad. Sci. USA, vol. 102, pp. 11070-11075, 2005.
Li et al., Symbiotic gut microbes modulate human metabolic phenotypes, Proc. Natl. Acad. Sci. USA, vol. 105, pp. 2117-2122, 2008.
Paulino et al., Molecular Analysis of Fungal Microbiota in Samples from Healthy Human Skin and Psoriatic Lesions, J Clin Microbiol, vol. 44, pp. 2933-2941, 2006.
Ray, Adding weight to the microbiota's role in obesity-exposure to antibiotics early in life can lead to increased adiposity, Nature Reviews/Gastroenterology & Hepatology, vol. 9, 2012.
Trasande et al, Infant antibiotic exposures and early-life body mass, International Journal of Obesity, advance online publication, Aug. 21, 2012, pp. 1-8; doi:10.1038/ijo.2012.132.
Turnbaugh et al., An obesity-associated gut microbiome with increased capacity for energy harvest, Nature, vol. 444, pp. 1027-1031, 2006.
Wade, Unculturable bacteria—the uncharacterized organisms that cause orl infections, Journal of The Royal Society of Medicine, vol. 95, pp. 81-83, 2002.
Wen et al., Innate immunity and intestinal microbiota in the development of Type 1 diabetes, Nature, vol. 455, pp. 1109-1113, 2008.
Wilson et al., Applications of molecular ecology in the characterization of uncultured microorganisms associated with human disease, Reviews in Medical Microbiology, vol. 8, pp. 91-101, 1997.
Written Opinion of International Searching Authority issued in International Appl. No. PCT/US2009/058351, dated May 10, 2010.
Written Opinion of International Searching Authority issued in International Appl. No. PCT/US2011/048501, dated Mar. 13, 2012.
Bjursell et al. "Functional Genomic and Metabolic Studies of the Adaptations of a Prominent Adult Human Gut Symbiont, Bacteroides thetaiotaomicron, to the Suckling Period" Journal of Biological Chemistry, 2006, 281:36269-36279.
Brandt et al. "An overview of fecal microbiota transplantation: techniques, indications, and outcomes" Gastrointestinal Endoscopy, 2013, 78(2):240-249.
Costello et al. "Bacterial Community Variation in Human Body Habitats Across Space and Time" Science, 2009, 326:1694-7.
Cox, M. J. et al. Lactobacillus casei Abundance is Associated with Profound Shifts in the Infant Gut Microbiome. PLoS ONE 5(1), e8745, doi:10.1371/journal.pone.0008745 (2010).
Gori et al. "Specific prebiotics modulate gut microbiota and immune activation in HAART adults: results of the 'COPA' pilot randomized trial," Nature, 2011, vol. 4, No. 5 (554-563).
Greenblum et al. "Metagenomic systems biology of the human gut microbiome reveals topological shifts associated with obesity and inflammatory bowel disease" Proc Natl Acad Sci, 2012, 109(2):594-599.
Grice et al. "Topographical and Temporal Diversity of the Human Skin Microbiome" Science, 2009, 324:1190-2.
Hamarajata, P. & Versalovic, J. Effects of probiotics on gut microbiota: mechanism of intestinal immunomodulation and neuromodulation. Therapeutic Advances in Gastroenterology 6(1), 39-51, doi:10.1177/1756283X12459294 (2013).
International Search Report and Written Opinion issued on Jan. 9, 2015 during prosecution of International Patent Application No. PCT/US2014/041770.
Kwok, L. et al. The impact of oral consumption of Lactobacillus plantarum P-8 on faecal bacteria revealed by pyrosequencing. Beneficial Microbes, 6(4), 405-413 (2015).
Mahowald et al. "Characterizing a model human gut microbiota composed of members of its two dominant bacterial phyla" Proc Natl Acad Sci, 2009, 106(14):5859-5864.
Marques et al. "Expression and functional importance of innate immune receptors by intestinal epithelial cells," Cell Mol Life Sci, 2011, vol. 68, Iss. 22 (3661-3673).
O'Hara et al. "The gut flora as a forgotten organ" European Molecular Biology Organiation, 2006, 7(7):688-693.
O'Toole, P. W. & Cooney, J. C. Probiotic Bacteria Influence the Composition and Function of the Intestinal Microbiota. Interdisciplinary Perspectives on Infectious Diseases, 1-9, doi:10.1155/2008/175285 (2008).
Pieper, R. et al. Effect of a single oral administration of Lactobacillus plantarum DSMZ 8862/8866 before and at the time point of

(56) References Cited

OTHER PUBLICATIONS weaning on intestinal microbial communities in piglets. International Journal of Food Microbiology 130, 227-232, doi:10.1016/j.ijfoodmicro.2009.01.026 (2009).
Qin et al. "A human gut microbial gene catalogue established by metagenomic sequencing" Nature, 2010, 464:59-67.
Rauch, M. & Lynch, S. Probiotic manipulation of the gastrointestinal microbiota. Gut Microbes 1(5), 335-338, doi:10.4161/gmic.1.5.13169 (2010).
Van Nood et al. "Duodenal Infusion of Donor Feces for Recurrent Clostridium difficile" New England Journal of Medicine, 2013, 368(5):407-415.
Wikoff et al. "Metabolomics analysis reveals large effects of gut microflora on mammalian blood metabolites" Proc Natl Acad Sci, 2009, 106(10):3698-3703.
Turta O. and Rautava S., (2016) "Antibiotics, obesity and the link to microbes—what are we doing to our children?" BMC Medicine, 14:57.
Sifferlin A., (2014) "Antibiotics in Early Life Can Lead to Weight Gain in Mice, Study Shows" Time Magazine, http://time.com/3111864/antibiotics-weight-gain-mice/.
Brugman S. et al., (2006) "Antibiotic treatment partially protects against type 1 diabetes in the Bio-Breeding diabetes-prone rat. Is the gut flora involved in the development of type 1 diabetes?" Diabetologia, 49:2105-2108.

\* cited by examiner

Quantitation Curve

Figure 16 C-D
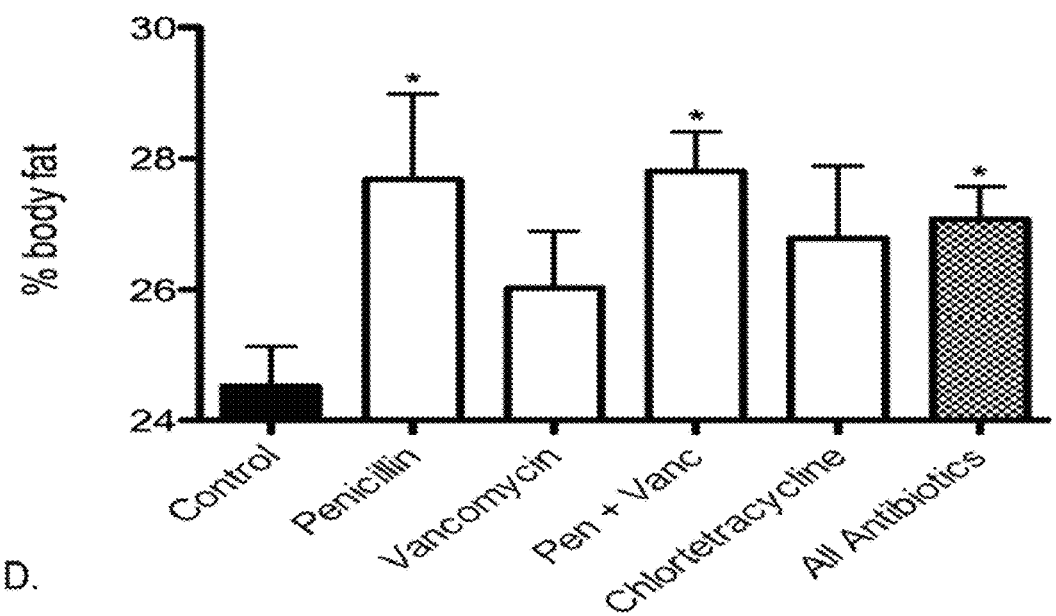
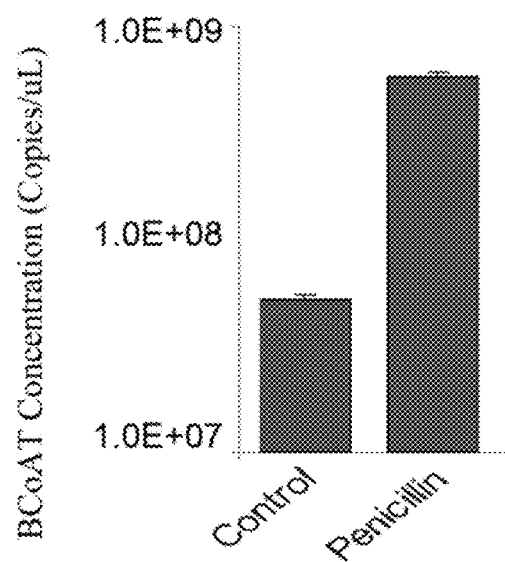

SEQUENCE LISTING

```
<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: primer

<400> SEQUENCE: 1
ccgcagccaa                                                            10

<210> SEQ ID NO 2
<211> LENGTH: 10
<212> TYPE: DNA
<213> ORGANISM: Artificial Sequence
<220> FEATURE:
<223> OTHER INFORMATION: primer

<400> SEQUENCE: 2
tgggcgtcaa                                                            10

<210> SEQ ID NO 3
<211> LENGTH: 10
<212> TYPE: DNA
<213> ORGANISM: Artificial Sequence
<220> FEATURE:
<223> OTHER INFORMATION: primer

<400> SEQUENCE: 3
gggcggtact                                                            10

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
actcctacgg gaggcagcag                                                 20

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
attaccgcgg ctgctgg                                                    17

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ctyggtcatt tagaggaagt aa                                              22

<210> SEQ ID NO 7
<211> LENGTH: 19
<212> TYPE: DNA
<213> ORGANISM: Artificial Sequence
```

<220> FEATURE:
<223> OTHER INFORMATION: primer

<400> SEQUENCE: 7
rctgcgttct tcatcgwtg                                                 19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
tcygtaggtg aacctgcrg                                                 19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agagtttgat ymtggctcag                                                20

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
tacggytacc ttgttacgac tt                                             22

<210> SEQ ID NO 11
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 11
gcngancatt tcacntggaa ywsntggcay atg                                 33

<210> SEQ ID NO 12
<211> LENGTH: 26
<212> TYPE: DNA
<213> ORGANISM: Artificial Sequence
<220> FEATURE:
<223> OTHER INFORMATION: primer
<220> FEATURE:

```
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (24)..(24)
<223> OTHER INFORMATION: n is a, c, g, or t

<400> SEQUENCE: 12
cctgcctttg caatrtcnac raangc                                          26
```

COMPOSITIONS AND METHODS FOR RESTORING GASTROINTESTINAL MICROBIOTA FOLLOWING ANTIBIOTIC TREATMENT

STATEMENT REGARDING FEDERALLY SPONSORED RESEARCH

Research and development leading to certain aspects of the present invention were supported, in part, by Grant No. UL1RR029893 awarded by the National Institutes of Health. Accordingly, the U.S. government may have certain rights in the invention. sp

CROSS REFERENCE TO RELATED APPLICATIONS

The present application claims priority to U.S. Provisional Patent Application Ser. No. 61/100,172, filed Sep. 25, 2008, and U.S. Provisional Patent Application Ser. No. 61/181,970, filed May 28, 2009, both of which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 1210469-US2.txt, and is approximately 2,296 bytes in size.

FIELD OF THE INVENTION

The present invention relates to characterizing changes in mammalian bacterial gastrointestinal, cutaneous (skin) and nasal microbiota associated with antibiotic treatment and various disease conditions (such as asthma, allergy, obesity, metabolic syndrome, insulin-deficiency or insulin-resistance related disorders, ischemia, oxidative stress, atherosclerosis, hypertension, abnormal lipid metabolism, gastrointestinal reflux disease (GERD), eosinophilic esophagitis, gastroesophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, etc.) and related diagnostic and therapeutic methods. Therapeutic methods of the invention involve the use of live bacterial inoculants that are capable of restoring healthy mammalian bacterial gastrointestinal, skin and nasal microbiota.

BACKGROUND OF THE INVENTION

It is estimated that between 20-25% of American adults (about 47 million) have metabolic syndrome, a complex condition associated with an increased risk of vascular disease. Metabolic syndrome is also known as Syndrome X, metabolic syndrome X, insulin resistance syndrome, or Reaven's syndrome. Metabolic syndrome is generally believed to be a combination of disorders that affect a large number of people in a clustered fashion. The symptoms and features of the syndrome include at least three of the following conditions: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity). Insulin resistance is typical of metabolic syndrome and leads to several of its features, including glucose intolerance, dyslipidemia, and hypertension. Obesity is commonly associated with the syndrome as is increased abdominal girth, highlighting the fact that abnormal lipid metabolism likely contributes to the underlying pathophysiology of metabolic syndrome.

Metabolic syndrome was codified in the United States with the publication of the National Cholesterol Education Program Adult Treatment Panel III (ATP III) guidelines in 2001. On a physiologic basis, insulin resistance appears to be responsible for the syndrome. However, insulin resistance can be defined in a myriad of different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation, all of which have been implicated in the cardiovascular disease associated with metabolic syndrome. At least at present, there is no obvious molecular mechanism causing the syndrome, probably because the condition represents a failure of one or more of the many compensatory mechanisms that are activated in response to energy excess and the accumulation of fat.

According to ATP III, the diagnosis of metabolic syndrome requires the presence of three or more of the following: elevated fasting triglycerides (greater than or equal to 150 mg/dl), low HDL cholesterol (less than 50 mg/dl in women, less than 40 mg/dl in men), hypertension (blood pressure greater than or equal to 130/85 mm Hg), increased waist circumference (due to excess visceral adiposity, greater than 35 inches in women, greater than 40 inches in men) and elevated fasting glucose (greater than or equal to 100 mg/dl). The presence of three components is not a perfect predictor of insulin resistance, and the World Health Organization has established somewhat different criteria that include microalbuminuria (i.e., slightly elevated albumin excretion in the urine), and some groups modify the ATP III criteria to include a body mass index (BMI) of greater than or equal to 30 kg/M$^2$ and abnormal nonfasting glucose and lipid values. Regardless of the definition, the syndrome identifies a group of individuals at increased risk for vascular disease. In an analysis of the Third National Health and Nutrition Examination Survey (NHANES III) participants over the age of 50 with metabolic syndrome showed a coronary heart disease prevalence exceeding that of diabetes. NHANES II data indicate total mortality as well as death from coronary heart disease and cardiovascular disease are increased in adults with metabolic syndrome.

Individuals at risk for metabolic syndrome include those who exhibit central obesity with increased abdominal girth (due to excess visceral adiposity) of about more than 35 inches in women and more than 40 inches in men. Individuals at risk for metabolic syndrome also include those that have a BMI greater than or equal to 30 kg/m$^2$ and may also have abnormal levels of nonfasting glucose, lipids, and blood pressure.

Obesity has become widespread with increases in prevalence across all developed nations (Bouchard, C (2000) N Engl J Med. 343, 1888-9). According to the Center for Disease Control (CDC), over 60% of the United States population is overweight, and greater than 30% are obese. For affected persons, the problem often begins in childhood, and continues for life. Major contributors are believed to be increased consumption of high calorie foods and a more sedentary life style. However, neither of these alone or together are sufficient to explain the rise in obesity and subsequent or concomitant obesity-related disorders, such as, e.g., type II diabetes mellitus, metabolic syndrome, hypertension, cardiac pathology, and non-alcoholic fatty liver disease. According to the National Institute of Diabetes, Digestive and Kidney Diseases (NIDDK) approximately 280,000 deaths annually are directly related to obesity. The NIDDK further estimated that the direct cost of healthcare in the U.S. associated with obesity is $51 billion. In addition, Americans spend $33 billion per year on weight loss products. The prevalence of obesity continues to rise at alarming rates.

Gastrointestinal reflux disease (GERD) and related disorders including Barrett's esophagus (BE), adenocarcinoma of the esophagus (EAC), and adenocarcinoma of the gastric cardia, (which collectively can be termed gastro-esophageal junction adenocarcinomas (GEJAC), are also becoming increasingly important medical problems in the United States and other developed countries. For affected persons, the problem often begins in childhood, but more typically presents clinically in adulthood, and continues for life. These disorders have become widespread with increases in incidence and prevalence across all developed nations. The rise in the problem has been so rapid that the major effect must be environmental, and not genetic. Major contributors are believed to be exposure to excess gastric acidity and particular foods and medications. However, none of these can fully explain the rise in GERD and its related conditions across widespread population groups. An alternative explanation is that the GERD is due to the growing epidemic of obesity, but since many non-obese persons suffer from GERD, this also is insufficient to explain the explosive rise in GERD and related esophageal diseases.

Similarly, childhood-onset asthma and related disorders including allergic rhinitis ("hay fever") and eczema (atopic dermatitis) are also becoming increasingly important medical problems in the United States and other developed countries. Asthma and related disorders have become widespread with increases in prevalence across all developed nations. Major contributors are believed to be exposure to environmental irritants, such as air pollution, tobacco smoke, and allergens, such as insect populations, and environmental microbes. However, none of these are sufficient to explain the rise in asthma and its related conditions across widespread population groups. An alternative explanation is that the lack of exposures to environmental microbes, such as those found in soil, in pets, and in farm animals is responsible for the rise in asthma (often called the "hygiene hypothesis"), but this too is insufficient to explain the explosive rise in asthma, especially that which begins in early childhood.

Although certain bacterial associations have been examined for these conditions, the role of bacterial microbiota in ailments such as asthma, obesity, GERD and certain related cancers, all of which have been on the rise in the 21$^{st}$ century, has not been clearly understood or appreciated. Thus, there remains a need for methods for diagnosing, treating and preventing conditions such as asthma, obesity, metabolic syndrome, GERD, gastro-esophageal junction adenocarcinomas (GEJAC), and related disorders.

The average human body, consisting of about $10^{13}$ cells, has about ten times that number of microorganisms. The $\sim10^{14}$ microbes that live in and on each of our bodies belong to all three domains of life on earth—bacteria, archaea and eukarya. The major sites for our indigenous microbiota are the gastrointestinal tract, skin and mucosal surfaces such as nasal mucosa and vagina as well as the oropharynx. By far, the largest bacterial populations are in the colon. Bacteria make up most of the flora in the colon and 60% of the dry mass of feces. Probably more than 1000 different species live in the gut. However, it is probable that >90% of the bacteria come from less than 50 species. Fungi and protozoa also make up a part of the gut flora, but little is known about their activities. The skin also has a diverse microbiome, also with likely >1000 species, yet with major populations within a small number of species (Gao et al., Proc. Natl. Acad. Sci. USA 2007, 104(8):2927-2932). While the microbiota is highly extensive, it is barely characterized. Consequently, the Roadmap of the National Institutes of Health (NIH) includes the "Human Microbiome Project" to better characterize our microbial communities and the genes that they harbor (our microbiome) and better understand its relation to both human health and disease. Reviewed in Dethlefsen et al., Nature, 2007, 449:811-818; Turnbaugh et al., Nature, 2007, 449:804-810; Ley et al., Cell, 2006, 124:837-848.

Studies show that the relationship between gut flora and humans is not merely commensal (a non-harmful coexistence), but rather often is a mutualistic, symbiotic relationship. Although animals can survive with no gut flora, the microorganisms perform a host of useful functions, such as training the immune system, preventing growth of harmful species, regulating the development of the gut, fermenting unused energy substrates, metabolism of glycans and amino acids, synthesis of vitamins (such as biotin and vitamin K) and isoprenoids, biotransformation of xenobiotics, and producing hormones to direct the host to store fats. See, e.g., Gill et al., Science. 2006, 312:1355-1359; Zaneveld et al., Curr. Opin. Chem. Biol., 2008, 12(1):109-114; Guarner, Digestion, 2006, 73:5-12; Li et al., Proc. Natl. Acad. Sci. USA, 2008, 105:2117-2122; Hooper, Trends Microbiol., 2004, 12:129-134; Mazmanian et al., Cell, 2005, 122:107-118; Rakoff-Nahoum et al., Cell, 2004, 118:229-241. It is therefore believed that changes in the composition of the gut microbiota could have important health effects (Dethlefsen et al., PLoS Biology, 2008, 6(11):2383-2400). Indeed, a correlation between obesity and changes in gut microbiota has been observed (Ley et al., Proc Natl Acad Sci USA, 2005; 102:11070-11075; Bäckhed et al., Proc Natl Acad Sci USA, 2004; 101:15718-15723). Furthermore, in certain conditions, some microbial species are thought to be capable of directly causing disease by causing infection or increasing cancer risk for the host (O'Keefe et al., J. Nutr. 2007; 137:175S-182S; McGarr et al., J Clin Gastroenterol., 2005; 39:98-109).

Substantial number of species in vertebrate microbiota is very hard to culture and analyze via traditional cultivation-based studies (Turnbaugh et al., Nature, 2007, 449:804-810; Eckburg et al., Science, 2005, 308:1635-1638). In contrast, broad-range PCR primers targeted to highly conserved regions makes possible the amplification of small subunit rRNA gene (16S rDNA) sequences from all bacterial species (Zoetendal et al., (2006) *Mol Microbial* 59, 1639-1650), and the extensive and rapidly growing 16S rDNA database facilitates identification of sequences to the species or genus level (Schloss and Handelsman, (2004) *Microbiol Mol Biol Rev* 68, 686-691). Such techniques can also be used for identifying bacterial species in complex environmental niches (Smit et al., (2001) *Appl Environ Microbiol* 67, 2284-2291), including the human mouth, esophagus, stomach, intestine, feces, skin, and vagina, and for clinical diagnosis (Harris and Hartley, (2003) *J Med Microbiol* 52, 685-691; Saglani et al., (2005) *Arch Dis Child* 90, 70-73).

Much of the microbiota is conserved from human to human, at least at the level of phylum and genus (for a general description of human microbiota see, e.g., Turnbaugh et al., Nature 2007; 449:804-810; Ley et al., Nature 2006; 444:1022-1023; Gao et al., Proc Natl Acad Sci USA 2007; 104:2927-32; Pei et al., Proc Natl Acad Sci USA 2004; 101:4250-4255; Eckburg et al., Science 2005; 308:1635-1638; Bik et al., Proc Natl Acad Sci USA 2006; 103:732-737). A major source of the human microbiota is from one's mother (for a summary of typical maternal colonization patterns see, e.g., Palmer et al., Plos Biology 2007; 5:e177; Raymond et al., Emerg Infect Dis 2004; 10:1816-21), and to a lesser extent from one's father and siblings (for examples of typical colonization patterns see, e.g., Raymond et al., Emerg Infect Dis 2004; 10:1816-21; Raymond et al., Plos One 2008; 3:e2259; Goodman et al., Am J Epidemiol 1996; 144:290-299; Goodman et al., Lancet 2000; 355:358-362). However, many of the natural mechanisms for the transmission of these indigenous organisms across generations and between family members have diminished with socioeconomic development. The impediments include: childbirth by caesarian section, reduced breast-feeding, smaller family size (fewer siblings), reduced household crowding with shared beds, utensils, in-door plumbing.

Effective antibiotics were discovered in the early-mid 20th century and came into wide use after World War II. Antibiotic use has increased dramatically with rates approximating one course of antibiotics per year in the average child in the USA (for a summary of US antibiotic courses in a year, see, e.g., McCaig et al., JAMA 2002; 287:3096-3102).

Antibiotic use places selective pressure on the microbiota, in particular selecting for the long-term persistence of resistant organisms (such persistence is described in Levy, Sci Am 1998; 278:46-53). Antibiotic resistance may be intrinsic or secondary to acquired genetic elements, but marker organisms (and genes) may be used to observe the phenomenon (examples of such markers may be found in, e.g., Sjölund et al., Annals of Internal Medicine 2003; 139: 483-487; Sjölund et al., Emerging Infectious Diseases 2005: 11:1389-1393).

Increased exposure to antibiotics in the first year of life has been associated with increased risk of developing asthma by seven years of age (Kozyrskyj et al., Chest. 2007; 131:1753-9). The effects are not specific to a single class of antibiotics, but involve many different agents. Additionally, the risk of asthma and related disorders has previously been inversely associated with the risk of having gastric colonization by *H. pylori*, as ascertained from serological tests (see, e.g., Reibman et al., Presented at ATS 2005; Chen and Blaser, Arch Intern Med 2007; 167:821-827; Chen and Blaser, J. Infect. Dis. 2008; 198:553-60; Blaser et al., Gut 2008; 57:561-7). The risk appears primarily limited to childhood onset asthma and related conditions.

The acute effects of antibiotic treatment on the native gut microbiota range from self-limiting "functional" diarrhea to life-threatening pseudomembranous colitis (Beaugerie and Petit, Best Pract Res Clin Gastroenterol. 2004; 18:337-352; Wilcox, Best Pract Res Clin Gastroenterol. 2003; 17:475-493). The long-term consequences of such perturbations for the human-microbial symbiosis are more difficult to discern, but chronic conditions such as asthma and atopic disease have been associated with childhood antibiotic use and an altered intestinal microbiota (see, e.g., Marra et al.; Chest. 2006; 129:610-618; Noverr and Huffnagle, Clin Exp Allergy. 2005; 35:1511-1520; Prioult and Nagler-Anderson; Immunol Rev. 2005; 206:204-218).

It has been known for more than 50 years that the administration of low doses of antibiotics promotes the growth of farm animals. As a result, the largest use of antibiotics and other antimicrobial substances is on the farm, where they are fed in low doses to large numbers of animals used for food production. Additionally, the following observations regarding antibiotic use are appreciated:

1. feeding low (subtherapeutic) doses of antimicrobials promotes weight gain (often 5-10% of total weight) of animals used for food production (See, e.g., Jukes, Bioscience 1972; 22: 526-534; Jukes (1955) Antibiotics in Nutrition. New York, N.Y., USA: Medical Encyclopedia; Feighner and Dashkevicz, Appl. Environ. Microbiol., 1987, 53: 331-336; McEwen and Fedorka-Cray, Clin. Infect. Dis., 2002, 34 (Suppl 3): S93-S106);
2. the effects are broad across vertebrate species, involving at least mammals (cattle, swine, sheep), and birds (chickens and turkeys);
3. the effects can be realized by oral administrations of the agents, suggesting that the microbiota of the gastrointestinal tract is a major target;
4. the effects are due to many different classes of antimicrobial agents (including macrolides, tetracyclines, penicillins);
5. anti-fungal agents do not produce the effect;
6. the effects can be observed at many different stages in the growth and development of young animals.

The mechanism for this widespread phenomenon has not been established but because of the activity of anti-bacterial but not anti-fungal agents, it can be ascertained to be anti-bacterial.

The vertebrate gastrointestinal tract has a rich component of cells involved in immune responses. The nature of the microbiota colonizing experimental animals or humans affects the immune responses of the populations of reactive host cells (see, e.g., Ando et al., Infection and Immunity 1998; 66:4742-4747; Goll et al., Helicobacter. 2007; 12:185-92; Lundgren et al., Infect Immun. 2005; 73:523-531).

The vertebrate gastrointestinal tract also is a locus in which hormones are produced. In mammals, many of these hormones related to energy homeostasis (including insulin, glucagon, leptin, and ghrelin) are produced by organs of the gastrointestinal tract (see, e.g., Mix et al., Gut 2000; 47:481-6; Kojima et al., Nature 1999; 402:656-60; Shak et al., Obesity Surgery 2008; 18(9):1089-96; Roper et al., Journal of Clinical Endocrinology & Metabolism 2008; 93:2350-7; Francois et al., Gut 2008; 57:16-24; Cummings and Overduin, J Clin Invest 2007; 117:13-23; Bado et al., Nature 1998; 394:790-793).

Changing of the microbiota of the gastrointestinal tract appears to affect the levels of some of these hormones (see, e.g., Breidert et al., Scand J Gastroenterol 1999; 34:954-61; Liew et al., Obes. Surg. 2006; 16:612-9; Nwokolo et al., Gut. 2003; 52, 637-640; Kinkhabwala et al., Gastroenterology 132:A208). The hormones affect immune responses (see, e.g., Matarese et al., J Immunol 2005; 174:3137-3142; Matsuda et al., J. Allergy Clin. Immunol. 2007; 119, S174) and adiposity (see, e.g., Tschop et al., Nature 2000; 407: 908-13).

SUMMARY OF THE INVENTION

As specified in the Background section above, there is a great need in the art (i) to understand the impact that mammalian bacterial microbiota has on the host health and (ii) to employ such knowledge in development of new therapeutics. There is further a great need in the art to treat such diseases as asthma, obesity, metabolic syndrome, insulin-deficiency or insulin-resistance related disorders, ischemia, oxidative stress, atherosclerosis, hypertension, abnormal lipid metabolism, gastrointestinal reflux disease (GERD), eosinophilic esophagitis, gastro-esophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, and related disorders.

The present invention addresses these and other needs by characterizing specific changes in mammalian bacterial microbiota associated with antibiotic treatment and specific diseases and related diagnostic and therapeutic methods.

In one aspect, the invention provides methods for determining the identity of antibiotic-depleted and antibiotic-enriched bacteria in mammalian microbiota by (i) screening 16S rRNA genes using PCR and by (ii) high-throughput sequencing methods (e.g., pyrosequencing, etc.), which detect over- and under-represented genes in the total bacterial population. In a related aspect, the present invention characterizes specific changes in mammalian bacterial gastrointestinal microbiota (on the phylum, class, order, family, genus, and species level which occur upon treatment with sub-therapeutic doses of antibiotics, wherein such treatment is associated with (i) increased % body fat and adipose tissue deposition and with (ii) increased bone mineral density (BMD) at early stages of life. Such specific antibiotic and/or obesity- and/or BMD-associated changes in mammalian bacterial gastrointestinal microbiota disclosed herein constitute diagnostics which can be used to determine whether a given mammal is likely to develop obesity and/or short stature.

In one specific embodiment, the invention provides that the ratio of the phyla Bacteroidetes to Firmicutes (B/F ratio) is decreased in mammalian bacterial gastrointestinal microbiota upon treatment with sub-therapeutic doses of antibiotics, wherein such treatment is associated with increased % body fat and adipose tissue deposition. Thus, the present invention provides a diagnostic of obesity based on screening for decreased B/F ratio in mammalian bacterial gastrointestinal microbiota, for example, using real-time (quantitative) PCR, and/or high throughput sequencing.

In another specific embodiment, the invention provides that the total number of Butyryl CoA transferase (BCoAT)—encoding genes (i.e., genes encoding an enzyme involved in the regulation of metabolism of short chain fatty acids and specifically butyrate synthesis) is increased in mammalian bacterial gastrointestinal microbiota upon treatment with sub-therapeutic doses of antibiotics, wherein such treatment is associated with increased % body fat and adipose tissue deposition. Thus, the present invention provides a diagnostic of obesity based on screening for increased number of Butyryl CoA transferase (BCoAT)—encoding genes (or other genes encoding an enzyme involved in the regulation of metabolism of short chain fatty acids (SCFA) and, preferably, butyrate synthesis) in mammalian bacterial gastrointestinal microbiota.

In yet another specific embodiment, the invention provides that the level of gastric inhibitory polypeptide (GIP) is increased in serum of a mammal upon treatment with sub-therapeutic doses of antibiotics, wherein such treatment is associated with increased % body fat and adipose tissue deposition. Thus, the present invention provides a diagnostic of obesity based on screening for increased GIP level in serum (e.g., using such methods as immunoassay).

In conjunction with diagnostic methods, the present invention also provides therapeutic methods for treating obesity and associated disorders (such as type II diabetes mellitus, metabolic syndrome, hypertension, cardiac pathology, non-alcoholic fatty liver disease, etc.) by restoring mammalian bacterial gastrointestinal microbiota to the composition observed in healthy subjects.

In a more general aspect, the present invention provides a method for treating various diseases associated with changes in gastrointestinal, cutaneous (skin), or nasal microbiota by restoring such microbiota to the composition observed in healthy subjects. Non-limiting examples of the diseases treatable by the methods of the present invention include asthma, allergy, obesity, metabolic syndrome, insulin-deficiency or insulin-resistance related disorders, ischemia, oxidative stress, atherosclerosis, hypertension, abnormal lipid metabolism, gastrointestinal reflux disease (GERD), eosinophilic esophagitis, gastro-esophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, and related disorders.

In certain specific embodiments, restoring of microbiota is achieved by administering to a mammal in need thereof a therapeutically effective amount of a probiotic composition comprising an effective amount of at least one bacterial strain, or a combinations of several strains, wherein the composition (i) stimulates or inhibits specific metabolic pathways involved in host energy homeostasis and/or (ii) stimulates growth and/or activity of bacteria which are under-represented in a disease and/or (iii) inhibits growth and/or activity of bacteria which are over-represented in a disease. Such bacterial strains administered according to the methods of the present invention can comprise live bacteria or conditional lethal bacteria, which survive for a limited time (e.g., when provided certain nutritional supplements). Bacterial strains useful in the methods of the invention encompass both disease-associated strains isolated from microbiota and "bacterial analogues", such as recombinant carrier strains expressing one or more heterologous genes derived from the bacteria affected in a disease. In certain embodiments, the bacterial inoculant used in the methods of the invention further comprises a buffering agent, such as, e.g., sodium bicarbonate, milk, yoghurt, infant formula, and other dairy products.

In certain embodiments, the present invention relates to a method for restoring mammalian bacterial gastrointestinal microbiota comprising administering to a mammal in need of such treatment, an effective amount of at least one gastric, esophageal, or colonic bacteria, or combinations thereof. In a preferred embodiment, the bacteria is administered orally. Alternatively, bacteria can be administered rectally or by enema.

In certain embodiments, the gastric bacteria administered in the therapeutic methods of the invention is *Helicobacter pylori*. Non-limiting examples of *H. pylori* strains useful in the methods of the invention include live or conditionally lethal cagA positive (cagA+) strains (i.e., strains possessing a full functioning cag island-encoded type IV secretion system that can inject the CagA protein and other *H. pylori* constituents into epithelial cell), live or conditionally lethal cagA negative (cagA−) strains, as well as live or conditionally lethal strains varying in VacA activity (of genotypes s1 or s2, m1 or m2, i1 or i2) and/or in expression of the type I or type II Lewis antigen pathways In certain embodiments, the bacteria administered in the therapeutic methods of the invention comprise *H. pylori* and one or more additional bacterial strains such as, e.g., *Oxalobacter* or *Lactobacillus* species. In one embodiment, the invention provides a method for treating asthma, allergy, gastrointestinal reflux disease (GERD), eosinophilic esophagitis, and related disorders in a mammal comprising administering to the mammal a therapeutically effective amount of *H. pylori* live or conditionally lethal cagA positive (cagA +) strain.

In certain embodiments, the probiotic composition of the invention comprises a therapeutically effective amount of at least one bacterial strain, or combinations of several strains, wherein the composition inhibits the growth of antibiotic-resistant bacteria. In a specific embodiment, such composition comprises one or several antibiotic-sensitive bacterial strains which have been diminished or lost as a result of antibiotic treatment. In one embodiment, such antibiotic-sensitive bacteria are capable of competing with antibiotic-resistant bacteria that facilitate calorie uptake in the gut and in this way lower weight gain by the host and treat obesity, metabolic syndrome, diabetes, and related disorders. In another embodiment, such antibiotic-sensitive bacteria are capable of competing with antibiotic-resistant bacteria and facilitate T regulatory responses in gastric and/or intestinal tissue and in this way treat asthma, allergy and related disorders (e.g., eczema, allergic rhinitis, etc.).

In certain embodiments, the invention relates to a method for restoring mammalian bacterial nasal microbiota comprising administering to a mammal in need of such treatment an effective amount of at least one nasal bacterial strain or a combination of several strains. Preferably, such nasal bacteria is administered intranasally. Non-limiting examples of the nasal bacteria useful in the methods of the invention include coagulase-negative *Staphylococcus* species, non-Group A *Streptococcus* species (non-GAS), and *Corynebacterium* species. Administration of such bacteria to nasal mucosa may be used to treat various infections, including infection with Methicillin-resistant *Staphylococcus aureus* (MRSA).

In certain embodiments, the invention relates to a method for restoring mammalian bacterial cutaneous (skin) microbiota comprising administering to a mammal in need of such treatment an effective amount of at least one cutaneous bacterial strain or a combination of several strains. Preferably, such cutaneous bacteria is administered topically. Non-limiting examples of the cutaneous bacteria useful in the methods of the invention include coagulase-negative *Staphylococcus* species, non-Group A *Streptococcus* species (non-GAS), *Corynebacterium* species, and *Propionibacteria* species. Administration of such bacteria to skin may be used to treat various diseases, including psoriasis and atopic dermatitis.

In certain other specific embodiments, the therapeutic methods of the invention rely on the administration of a therapeutically effective amount of a prebiotic agent or a combination of such agents that (i) increase the number and/or activity of one or more bacteria which are under-represented in a disease and/or (ii) decrease the number and/or activity of one or more bacteria which are over-represented in a disease. Non-limiting examples of prebiotic agents useful in the methods of the present invention include fructooligosaccharides (e.g., oligofructose, inulin, and inulin-type fructans), galactooligosaccharides, amino acids, alcohols, and mixtures thereof.

In certain other specific embodiments, the therapeutic methods of the invention rely on the administration of a therapeutically effective amount of a naturally or recombinantly produced bacterial protein or a combination of such proteins which (i) increase the number and/or activity of one or more bacteria which are under-represented in a disease and/or (ii) decrease the number and/or activity of one or more bacteria which are over-represented in a disease. The proteins according to this embodiment may be produced by the same strain of bacteria which is intended to be regulated or by a different strain.

In certain embodiments, the invention provides a method for restoring gastrointestinal, cutaneous, or nasal microbiota in a subject depleted as a result of antibiotic treatment or disease comprising:
 a) identifying under-represented bacterial species in an antibiotic-treated or diseased microbiota sample from the subject as compared to a control untreated/healthy sample;
 b) culturing the identified under-represented bacteria from step a); and
 c) administering the bacterial inoculant(s) from step b) to the subject, wherein the inoculant(s) increases growth of the under-represented bacteria in the subject.

In certain embodiments, the invention provides a method for restoring a function of gastrointestinal, cutaneous, or nasal microbiota in a subject affected as a result of antibiotic treatment or disease comprising:
 a) determining the metagenome of an antibiotic-treated or diseased microbiota sample from the subject;
 b) determining the metagenome of a control untreated/healthy sample;
 c) identifying under-represented and over-represented genes in the antibiotic-treated or diseased microbiota sample in relation to the control sample;
 d) selecting one or more bacterial strains to compensate for the expression of one or more genes identified in step c); and
 e) administering the bacterial inoculant of the one or more strains of step d) to the subject, wherein the inoculant restores the function of the antibiotic-treated or diseased microbiota to the untreated/healthy condition.

DETAILED DESCRIPTION OF THE INVENTION

Figure 1:
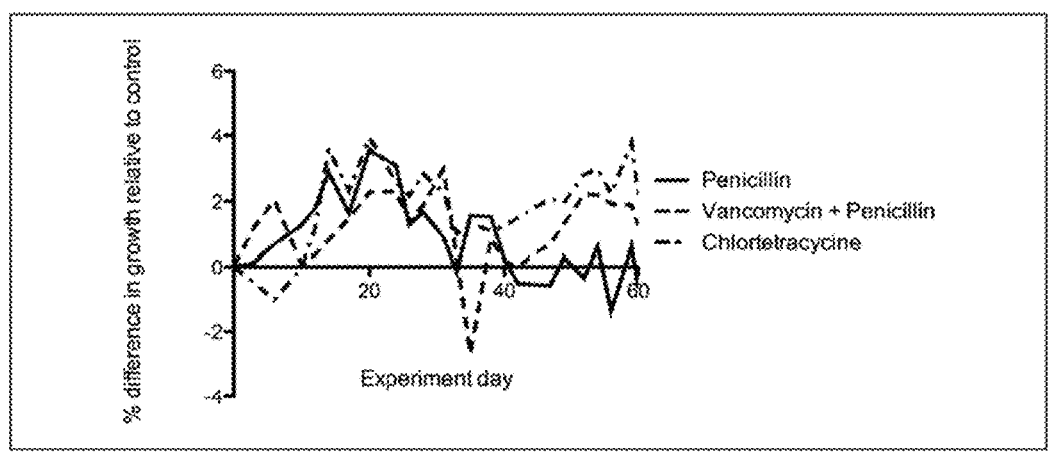
FIG. 1 shows a graph of the growth of sub-therapeutic antibiotic treated (STAT) mice in relation to control mice over the course of 60 days.

The present invention is based on a realization that an increased antibiotic use in humans and veterinary animals is associated with both (i) changes in the composition of the gastrointestinal microbiota and (ii) increased incidence of obesity, asthma, allergy, and esophageal reflux disorders. It is suggested herein that restoring the gastrointestinal microbiota to "pre-antibiotic" state offers potentially simple and practical therapeutic solution to the prevention and treatment of these diseases.

While not wishing to be bound by any particular theory, it is believed that changes in gastrointestinal bacteria cause the above diseases by affecting both immunological and hormonal functions of the host, which, in turn, affect the balance of energy consumption and storage and/or immunological homeostasis between tolerance and sensitization.

As specified in the Examples section, below, the present invention is based on unexpected observation that specific changes in bacterial gastrointestinal microbiota (on the phylum, class, order, family, genus, and species level) in mice occur upon treatment with sub-therapeutic doses of various antibiotics, wherein such treatment is associated with (i) increased % body fat and adipose tissue deposition and with (ii) increased bone mineral density (BMD) at early stages of life. For example, as disclosed in Example 1, below, the ratio of the phyla Bacteroidetes to Firmicutes (B/F ratio) is decreased in bacterial gastrointestinal microbiota of mice upon treatment with sub-therapeutic doses of penicillin and/or vancomycin, wherein such treatment is associated with increased % body fat and adipose tissue deposition. As further provided in Example 1, below, the total number of Butyryl CoA transferase (BCoAT)—encoding genes (i.e., genes encoding an enzyme involved in the regulation of metabolism of short chain fatty acids and specifically butyrate synthesis) is increased in bacterial gastrointestinal microbiota of mice upon treatment with sub-therapeutic doses of penicillin, wherein such treatment is associated with increased % body fat and adipose tissue deposition. As disclosed in Example 1, below, the level of gastric inhibitory polypeptide (GIP) is increased in serum of mice upon treatment with sub-therapeutic doses of various antibiotics, wherein such treatment is associated with increased % body fat and adipose tissue deposition.

As proposed herein, such specific antibiotic- and/or obesity- and/or BMD-associated changes in mammalian bacterial gastrointestinal microbiota disclosed herein constitute diagnostics which can be used to determine whether a given mammal is likely to develop obesity and/or short stature.

In conjunction with diagnostic methods, the present invention also provides therapeutic methods for treating obesity and associated disorders (such as type II diabetes mellitus, metabolic syndrome, hypertension, cardiac pathology, non-alcoholic fatty liver disease, etc.) by restoring mammalian bacterial gastrointestinal microbiota to the composition observed in healthy subjects. In a more general aspect, the present invention provides a method for treating various diseases associated with changes in gastrointestinal, cutaneous (skin), or nasal microbiota by restoring such microbiota to the composition observed in healthy subjects. Non-limiting examples of the diseases treatable by the methods of the present invention include asthma, allergy, obesity, metabolic syndrome, insulin-deficiency or insulin-resistance related disorders, ischemia, oxidative stress, atherosclerosis, hypertension, abnormal lipid metabolism, gastrointestinal reflux disease (GERD), eosinophilic esophagitis, gastro-esophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, and related disorders.

Definitions and Abbreviations

As used herein, the term "bacteria" encompasses both prokaryotic organisms and archaea present in mammalian microbiota.

The terms "intestinal microbiota", "gut flora", and "gastrointestinal microbiota" are used interchangeably to refer to bacteria in the digestive tract.

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, milk, yoghurt, infant formula, and other dairy products.

As used herein, the term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, amino acids, alcohols, and mixtures thereof. See, e.g., Ramirez-Farias et al., Br J Nutr (2008) 4:1-10; Pool-Zobel and Sauer, J Nutr (2007), 137:2580S-2584S.

As used herein, the term "metagenome" refers to genomic material obtained directly from a subject, instead of from culture. Metagenome is thus composed of microbial and host components.

The terms "treat" or "treatment" of a state, disorder or condition include:
(1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
(2) inhibiting the state, disorder or condition, i.e., arresting, reducing or delaying the development of the disease or a relapse thereof (in case of maintenance treatment) or at least one clinical or sub-clinical symptom thereof; or
(3) relieving the disease, i.e., causing regression of the state, disorder or condition or at least one of its clinical or sub-clinical symptoms.

The benefit to a subject to be treated is either statistically significant or at least perceptible to the patient or to the physician.

A "therapeutically effective amount" means the amount of a bacterial inoculant or compound that, when administered to a subject for treating a state, disorder or condition, is sufficient to effect such treatment. The "therapeutically effective amount" will vary depending on the compound, bacteria or analogue administered as well as the disease and its severity and the age, weight, physical condition and responsiveness of the mammal to be treated.

As used herein, the phrase "pharmaceutically acceptable" refers to molecular entities and compositions that are generally regarded as physiologically tolerable.

As used herein, the term "combination" of a bacterial inoculant, probiotic, analogue, or prebiotic compound and at least a second pharmaceutically active ingredient means at least two, but any desired combination of compounds can be delivered simultaneously or sequentially (i.e., within a 24 hour period).

"Patient" or "subject" as used herein refers to mammals and includes human and veterinary animals.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The abbreviations used in the nucleotide sequences throughout this application are as follows: A=adenine, G=guanine, C=cytosine, T=thymine, U=uracil, R=purine (G or A), Y=pyrimidine (T or U or C), M=amino (A or C), S=strong interactions 3H-bonds (G or C), W=weak interactions 2H-bonds (A or T or U), N=any (A or G or C or T or U), I=inosine.

Diagnostic Methods of the Invention

In certain aspects, the present invention relates generally to characterizing gastrointestinal, cutaneous or nasal microbiota under various conditions and comparing normal and diseased microbiota in order to determine a microbial signature for the desired condition. The microbiota can be characterized utilizing a broad range of molecular approaches. While any number of suitable molecular techniques may be utilized, particularly useful molecular techniques for the purposes of the present invention include (i) screening of microbial 16S ribosomal RNAs (16S rRNA) using PCR and (ii) high-throughput "metagenome" sequencing methods, which detect over- and under-represented genes in the total bacterial population. Screening of 16S rRNA genes permits characterizing microorganisms present in the microbiota at the species, genus, family, order, class, or phylum level. Such screening can be performed, e.g., by conducting PCR using universal primers to the V2, V3, V4, V6 (or V2-V4) region of the 16S rRNA gene followed by high-throughput sequencing and taxonomic analysis. See e.g., Gao et al. Proc. Natl. Acad. Sci. USA, 2007; 104:2927-32; Zoetendal et al., Mol. Microbiol., 2006, 59:1639-1650; Schloss and Handelsman, Microbiol. Mol. Biol. Rev., 2004, 68:686-691; Smit et al., Appl. Environ. Microbiol., 2001, 67:2284-2291; Harris and Hartley, J. Med. Microbial., 2003, 52:685-691; Saglani et al., Arch Dis Child, 2005, 90:70-73. The high-throughput "metagenome" sequencing methods involve obtaining multiple parallel short sequencing reads looking for under- and over-represented genes in a total mixed sample population. Such sequencing is usually followed by determining the G+C content or tetranucleotide content (Pride et al., Genome Res., 2003, 13; 145) of the genes to characterize the specific bacterial species in the sample. Additional techniques include those involving cultivation of individual microorganisms from mixed samples. See, e.g., Manual of Clinical Microbiology, 8th edition; American Society of Microbiology, Washington D.C., 2003.

In a related aspect, the present invention characterizes specific changes in mammalian bacterial gastrointestinal microbiota (on the phylum, class, order, family, genus, and species level) which occur upon treatment with sub-therapeutic doses of antibiotics, wherein such treatment is associated with (i) increased % body fat and adipose tissue deposition and with (ii) increased bone mineral density (BMD) at early stages of life. Such specific antibiotic and/or obesity-associated changes in mammalian bacterial gastrointestinal microbiota disclosed herein constitute diagnostics which can be used to determine whether a given mammal is likely to develop obesity and/or short stature.

In one embodiment, the present invention provides a diagnostic of obesity and related disorders based on screening for a decreased ratio of the phyla Bacteroidetes to Firmicutes (B/F ratio) in mammalian bacterial gastrointestinal microbiota. B/F ratio can be determined, for example, by determining the ratio of bacterial genomic sequences corresponding to each phyla using such methods as (i) screening of microbial 16S ribosomal RNAs (16S rRNA) using PCR and/or (ii) high-throughput sequencing.

In another embodiment, the present invention provides a diagnostic of obesity and related disorders based on screening for increased number of Butyryl CoA transferase (BCoAT)—encoding genes (or other genes encoding an enzyme involved in the regulation of metabolism of short chain fatty acids and, preferably, butyrate synthesis) in mammalian bacterial gastrointestinal microbiota.

The present invention also provides a diagnostic of obesity and related disorders based on screening for increased gastric inhibitory polypeptide (GIP) level in serum (e.g., using such methods as immunoassay).

Therapeutic Methods of the Invention

In conjunction with the diagnostic methods, the present invention also provides therapeutic methods for treating obesity and associated disorders (such as type II diabetes mellitus, metabolic syndrome, hypertension, cardiac pathology, non-alcoholic fatty liver disease, etc.) by restoring mammalian bacterial gastrointestinal microbiota to the composition observed in healthy subjects.

In a more general aspect, the present invention provides a method for treating various diseases associated with changes in gastrointestinal, cutaneous (skin), or nasal microbiota by restoring such microbiota to the composition observed in healthy subjects. Non-limiting examples of the diseases treatable by the methods of the present invention include asthma, allergy, obesity, metabolic syndrome, insulin-deficiency or insulin-resistance related disorders, ischemia, oxidative stress, atherosclerosis, hypertension, abnormal lipid metabolism, gastrointestinal reflux disease (GERD), eosinophilic esophagitis, gastro-esophageal junction adenocarcinomas (GEJAC), infections due to bacteria that are resistant to antibiotics, including Methicillin-resistant *Staphylococcus aureus* (MRSA), *Clostridium difficile*, vancomycin-resistant enterococci, and related disorders.

In certain specific embodiments, restoring of microbiota is achieved by administering to a mammal in need thereof a therapeutically effective amount of a probiotic composition comprising an effective amount of at least one bacterial strain, or a combinations of several strains, wherein the composition (i) stimulates or inhibits specific metabolic pathways involved in host energy homeostasis and/or (ii) stimulates growth and/or activity of bacteria which are under-represented in a disease and/or (iii) inhibits growth and/or activity of bacteria which are over-represented in a disease.

Bacterial strains administered according to the methods of the present invention can comprise live bacteria. One or several different bacterial inoculants can be administered simultaneously or sequentially (including administering at different times). Such bacteria can be isolated from microbiota and grown in culture using known techniques. However, many bacterial species are very difficult to culture and administration of others (like *H. pylori*) may lead to various undesirable side-effects. The present invention therefore comprises administering "bacterial analogues", such as recombinant carrier strains expressing one or more heterologous genes derived from the bacteria affected in a disease. The use of such recombinant bacteria may allow the use of lower therapeutic amounts due to higher protein expression and may simultaneously allow to avoid any potential harmful side-effects associated with reintroduction of specific bacterial strains. Non-limiting examples of recombinant carrier strains useful in the methods of the present invention include *E. coli* and *Lactobacillus* (e.g., *E. coli* and *Lactobacillus* expressing cag island-encoded type IV secretion system of *H. pylori*). Methods describing the use of bacteria for heterologous protein delivery are described, e.g., in U.S. Pat. No. 6,803,231.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria dies. Methods relating to conditional lethal strains of *H. pylori* are described in U.S. Pat. No. 6,570,004.

In certain embodiments, the bacterial inoculant used in the methods of the invention further comprises a buffering agent. Examples of useful buffering agents include sodium bicarbonate, milk, yoghurt, infant formula, and other dairy products.

Administration of a bacterial inoculant can be accomplished by any method likely to introduce the organisms into the desired location. The bacteria can be mixed with a carrier and (for easier delivery to the digestive tract) applied to liquid or solid food, or feed or to drinking water. The carrier material should be non-toxic to the bacteria and the subject/patient. Preferably, the carrier contains an ingredient that promotes viability of the bacteria during storage. The formulation can include added ingredients to improve palatability, improve shelf-life, impart nutritional benefits, and the like. If a reproducible and measured dose is desired, the bacteria can be administered by a rumen cannula.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacterial inoculant, e.g. $10^6$, $10^7$, $10^8$, $10^9$, and $10^{10}$ CFU for example, can be administered in a single dose. Lower doses can also be effective, e.g., $10^4$, and $10^5$ CFU. Similar doses can be used for administration to skin and nasal mucosa.

In certain embodiments, the present invention relates to a method for restoring mammalian bacterial gastrointestinal microbiota comprising administering to a mammal in need of such treatment, an effective amount of at least one gastric, esophageal, or colonic bacteria, or combinations thereof. In a preferred embodiment, the bacteria is administered orally. Alternatively, bacteria can be administered rectally or by enema.

One of the organisms contemplated for administration to restore the gastrointestinal microbiota is *Helicobacter pylori*. *H. pylori* is Gram-negative, microaerophilic, fastidious bacterium that colonizes specifically the surface of the mucosa of the stomach. Non-limiting examples of *H. pylori* strains useful in the methods of the invention include live or conditionally lethal cagA positive (cagA +) strains (i.e., strains possessing a full functioning cog island-encoded type IV secretion system that can inject the CagA protein and other *H. pylori* constituents into epithelial cell), live or conditionally lethal cagA negative (cagA−) strains, as well as live or conditionally lethal strains varying in VacA activity (of genotypes s1 or s2, m1 or m2, i1 or i2) and/or in expression of the type I or type II Lewis antigen pathways. In certain embodiments, the bacteria administered in the therapeutic methods of the invention comprise *H. pylori* and one or more additional bacterial strains (such as, e.g., *Oxalobacter* species, *Lactobacillus* species, etc.). In one embodiment, the invention provides a method for treating asthma, allergy, gastrointestinal reflux disease (GERD), eosinophilic esophagitis, and related disorders in a mammal comprising administering to the mammal a therapeutically effective amount of *H. pylori* live or conditionally lethal cagA positive (cagA +) strain.

In certain embodiments, the probiotic composition of the invention comprises a therapeutically effective amount of at least one bacterial strain, or combinations of several strains, wherein the composition inhibits the growth of antibiotic-resistant bacteria. In a specific embodiment, such composition comprises one or several antibiotic-sensitive bacterial strains which have been diminished or lost as a result of antibiotic treatment. In one embodiment, such antibiotic-sensitive bacteria are capable of competing with antibiotic-resistant bacteria that facilitate calorie uptake in the gut and in this way lower weight gain by the host and treat obesity, metabolic syndrome, diabetes, and related disorders. In another embodiment, such antibiotic-sensitive bacteria are capable of competing with antibiotic-resistant bacteria and facilitate T regulatory responses in gastric and/or intestinal tissue and in this way treat asthma, allergy, and related disorders (e.g., eczema, allergic rhinitis, etc.).

In certain embodiments, the invention relates to a method for restoring mammalian bacterial nasal microbiota comprising administering to a mammal in need of such treatment an effective amount of at least one nasal bacterial strain or a combination of several strains. Preferably, such nasal bacteria is administered intranasally. Non-limiting examples of the nasal bacteria useful in the methods of the invention include coagulase-negative *Staphylococcus* species, non-Group A *Streptococcus* species (non-GAS), and *Corynebacterium* species. Administration of such bacteria to nasal mucosa may be used to treat various infections, including infection with Methicillin-resistant *Staphylococcus aureus* (MRSA).

In certain embodiments, the invention relates to a method for restoring mammalian bacterial cutaneous microbiota comprising administering to a mammal in need of such treatment an effective amount of at least one cutaneous bacterial strain or a combination of several strains. Preferably, such cutaneous bacteria is administered topically. Non-limiting examples of the cutaneous bacteria useful in the methods of the invention include coagulase-negative *Staphylococcus* species, non-Group A *Streptococcus* species (non-GAS), *Corynebacterium* species, and *Propionibacteria* species. Administration of such bacteria to skin may be used to treat various diseases, including psoriasis and atopic dermatitis.

In certain other specific embodiments, the therapeutic methods of the invention rely on the administration of a therapeutically effective amount of a prebiotic agent or a combination of such agents that (i) increase the number and/or activity of one or more bacteria which are under-represented in a disease and/or (ii) decrease the number and/or activity of one or more bacteria which are over-represented in a disease. Non-limiting examples of prebiotic agents useful in the methods of the present invention include fructooligosaccharides (e.g., oligofructose, inulin, inulin-type fructans), galactooligosaccharides, amino acids, alcohols, and mixtures thereof. Additional prebiotic agents can be selected based on the knowledge of a particular microbiota-affected host metabolic pathway and/or immunological response implicated in a disease to be treated.

In certain other specific embodiments, the therapeutic methods of the invention rely on the administration of a therapeutically effective amount of a naturally or recombinantly produced bacterial protein or a combination of such proteins which (i) increase the number and/or activity of one or more bacteria which are under-represented in a disease and/or (ii) decrease the number and/or activity of one or more bacteria which are over-represented in a disease. The proteins according to this embodiment may be produced by the same strain of bacteria which is intended to be regulated or by a different strain.

Pharmaceutical Compositions

While it is possible to use a bacterial inoculant or compound of the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Although there are no physical limitations to delivery of the formulations of the present invention, oral delivery is preferred for delivery to the digestive tract because of its ease and convenience, and because oral formulations readily accommodate additional mixtures, such as milk, yoghurt, and infant formula. For delivery to colon, bacteria can be also administered rectally or by enema. Topical delivery is preferred, when the formulations of the invention are delivered to cutaneous microbiota. For delivery to nasal microbiota, preferred delivery route is intranasal.

Combination Treatments

For an enhanced therapeutic effect, the bacterial inoculants or compounds as described herein can be administered in combination with other therapeutic agents or regimes as discussed. The choice of therapeutic agents that can be co-administered with the bacterial inoculants or compounds of the invention depends, in part, on the condition being treated.

Non-limiting examples of additional pharmaceutically active compounds useful for treatment of obesity, metabolic syndrome, and related disorders such as insulin-deficiency or insulin-resistance related disorders, ischemia, oxidative stress, atherosclerosis, hypertension, abnormal lipid metabolism include anti-inflammatory agents, antioxidants, antiarrhythmics, cytokines, analgesics, vasodilators, antihypertensive agents including beta-blockers, angiotensin converting enzyme inhibitors (ACE inhibitors), and calcium channel blockers, inhibitors of cholesterol synthesis, antithrombotic agents, and diabetes drugs.

Examples of inhibitors of cholesterol synthesis or absorption which are useful in the combination therapies of the present invention include Hmg-CoA reductase inhibitors and their bio-active metabolites, such as, e.g., simvastatin, lovastatin, pravastatin, compactin, fluvastatin, dalvastatin, atorvastatin, HR-780, GR-95030, CI-981, BMY 22089, and BMY 22566. See, e.g., U.S. Pat. Nos. 4,346,227; 4,444,784; 4,857,522; 5,190,970; 5,316,765, and 5,461,039; PCT Publ. No. WO84/02131; GB Pat. No. 2,202,846. As used in the methods or compositions of the present invention, any one or several of the Hmg-CoA reductase inhibitor compounds may be mixed with L-arginine or a substrate precursor to endogenous nitric oxide, as described in U.S. Pat. Nos. 6,425,881 and 6,239,172, and 5,968,983, to provide a therapeutically effective mixture for use in conjunction with compounds of the present invention.

Non-limiting examples of diabetes drugs useful in the combination therapies of the present invention include insulin, proinsulin, insulin analogs, activin, glucagon, somatostatin, amylin, actos (pioglitazone), amaryl (glimepiride), glipizide, avandia (rosiglitazone), glucophage, glucotrol, glucovance (a combination of glyburide and metformin), and the like. See, e.g., U.S. Pat. No. 6,610,272. The term "insulin" encompasses natural extracted human insulin, recombinantly produced human insulin, insulin extracted from bovine and/or porcine sources, recombinantly produced porcine and bovine insulin and mixtures of any of these insulin products. In accordance with the present invention, administering a bacterial inoculant or compound of the present invention in combination with insulin is expected to lower the dose of insulin required to manage the diabetic patient, while also alleviating the symptoms of metabolic syndrome.

In accordance with, the present invention there may be numerous tools and techniques within the skill of the art, such as those commonly used in molecular immunology, cellular immunology, pharmacology, and microbiology. Such tools and techniques are describe in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

EXAMPLE 1

Analysis of Gastrointestinal Microbiota of Mice Treated with Sub-Therapeutic Levels of Antibiotics and Associated Metabolic Effects Animals
1. Mouse Species C57/B6 mice were obtained at weaning (21 days) from Jackson Laboratories (Bar Harbor, Me.). They were weighed and then distributed in cages so that the mean weights of the mice in each cage were equal. The mice were then allowed to adjust to the NYU animal facility. At day 23 of life, the antibiotic-exposure experiment began. Animals were allowed ad libitum access to food and water and maintained with a 12-hour light/dark cycle. The mice were fed standard laboratory chow (Purina Mills International Diet # 5001). These conditions were continued until the time of sacrifice.

2. Treatment Groups

Mice were given standard water (pH 6.8) or water containing the following antimicrobial agents (at sub-therapeutic levels) in groups of 5-10 mice per experimental condition.

TABLE 2

ANTIMICROBIAL AGENTS STUDIED

| Antimicrobial agent studied | Antimicrobial Class | Dosage administered $(\mu g/g)^a$ |
|---|---|---|
| Penicillin | Beta-lactam | 1.0 |
| Vancomycin | Glycopeptide | 1.0 |
| Penicillin + Vancomycin | As above | 1.0 + 1.0 |
| Chlortetracycline | Tetracycline | 1.0 |
| Bacitracin | Cyclic polypeptide | 1.0 |
| Ciprofloxacin | Fluoroquinolone | 1.0 |
| Tylosin | Macrolide | 1.0 |
| Virginiamycin | Streptogramin | 0.4 |

$^a$ = μg antimicrobial agent/g body weight of mice

3. Fecal/Cecal Specimens

At approximately weekly intervals, a fresh fecal pellet was collected from each individual mouse and frozen at −80° C. until DNA could be extracted. At the time of sacrifice, a fecal pellet was collected, as well as the cecal contents.

4. Calculations

Mouse Weights

Each mouse was weighed three days a week, twice each day on an electronic scale that was tared between all measurements. Each of the two weight measurements and the mean of the two measurements for each day were recorded. FIG. 1 shows cumulative growth of sub-therapeutic antibiotic treated (STAT) mice in relation to control mice, day 0 to day 60. The incremental growth of the STAT mice was expressed as a % difference relative to the control group, represented as the baseline. Mean daily weight gains for STAT mice were then normalized with reference to the control mice. STAT mice had a statistically significant increase in normalized weight gain when compared to the control mice.

Feed Weight

The amount of feed consumed by the mice in each cage was measured three days a week and the average daily feed intake was calculated and recorded.

Feed Efficiency

Feed efficiency was calculated by dividing the daily average weight gain by the daily mean feed consumed for each mouse. Feed efficiency was first calculated as the daily weight gain (g)/daily feed consumed (g). Feed efficiency calculations for the antimicrobial-exposed mice were then normalized with reference to the control mice. STAT mice had a 17.4% increase in feed efficiency when compared to the control mice.

5. Mouse Sacrifice

The mice were sacrificed through carbon dioxide asphyxiation. Immediately upon sacrifice, a thoracotomy and cardiac puncture to collect blood was performed. The blood was allowed to coagulate and then centrifuged to separate serum from whole cells. Cecal contents were collected and portions of the liver, ileum, and cecum were harvested. All serum and tissue samples were frozen and stored at −80° C. for future study.

6. Analysis of Body Composition

Body composition (fat mass, lean mass, percent [%] body fat) was determined using dual energy X-ray absorptiometry (DEXA) with a Lunar PIXImus II mouse densitometer (PIXImus, Fitchburg, Wis.) at the time of sacrifice. Each mouse was scanned individually. Data collected from the scan included fat and lean body mass, percent body fat, and bone mineral density. The results of these data are shown in FIGS. 2-5.

Figure 2A:
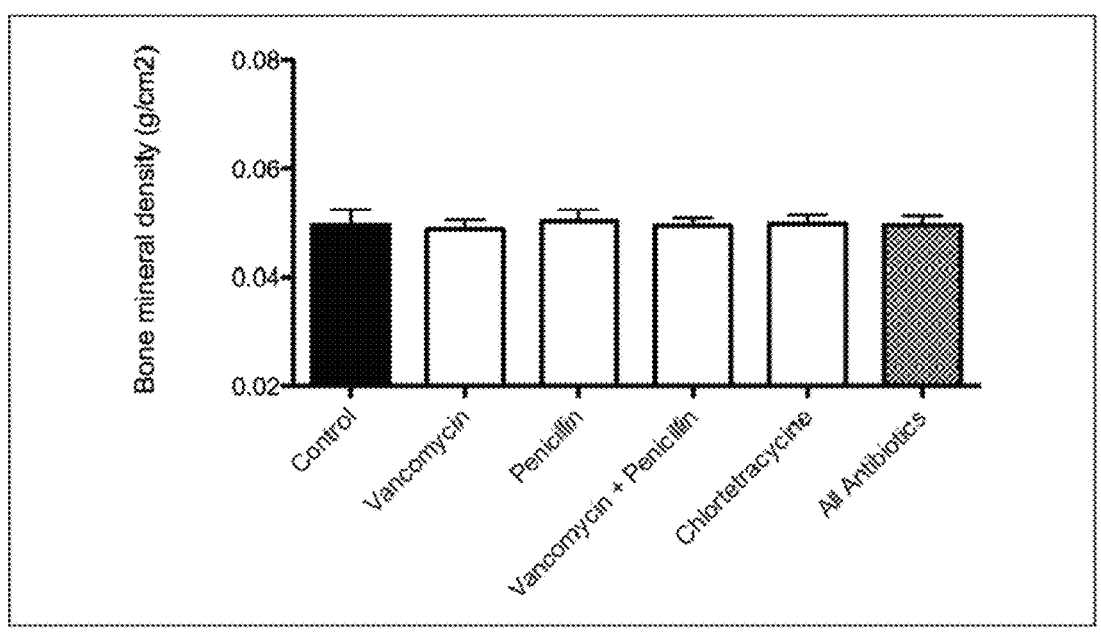
FIGS. 2A-B show a comparison of bone mineral density (BMD) between sub-therapeutic antibiotic treated (STAT) and control mice at day 63 of life (A) and at two weeks after weaning (B). The figure demonstrates that at two weeks after weaning, the STAT mice had a 6.6% increase in BMD as compared to the controls (*$p<0.05$ by Mann-Whitney U-test).
Figure 2B:
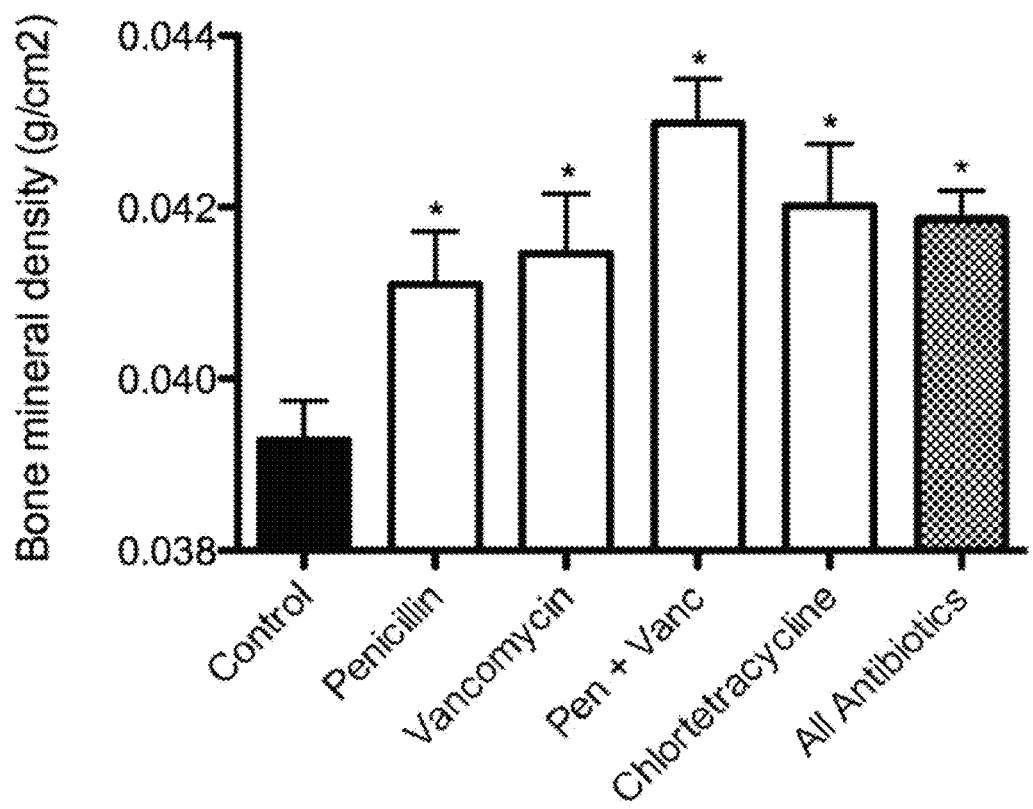

Since maximal growth of mice in these experiments was during the first 2 weeks after weaning, a group of mice were sacrificed at two weeks, and bone mineral density (BMD) and fat phenotypes assessed. FIGS. 2A-B show a comparison of BMD between sub-therapeutic antibiotic treated (STAT) and control mice at day 63 of life (A) and at two weeks after weaning (B). As shown in FIG. 2B, at two weeks after weaning, the STAT mice had a 6.6% increase in BMD as compared to the controls (*p<0.05 by Mann-Whitney U-test; with significant increases for each of the STAT regimens). At two weeks, there were no differences in lean muscle or fat mass between STAT and control mice. By 6-9 weeks of age, BMD was equivalent in all five groups of mice (FIG. 2A). These studies provide evidence of an early developmental effect in the STAT mouse models that is consistent with the growth promotion observed in farm animals treated with antibiotics. Specifically, these data provide evidence that STAT treatment affects the formation of bone, implying a role for the gut microbiota in bone development, and ultimately in the attainment of height. This implies that the early manipulation of the microbiota through replacement or inhibition can be used to prevent short stature.

Figure 3A:
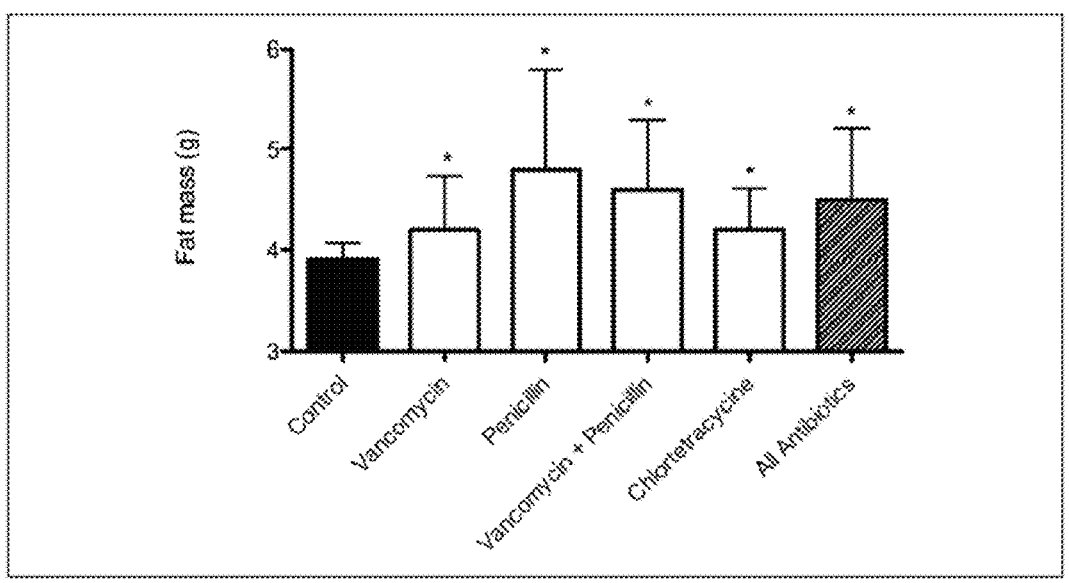
FIGS. 3A-B show (A) a comparison of fat mass between sub-therapeutic antibiotic treated (STAT) and control mice at the time of sacrifice (day 63) and (B) dual-energy X-ray absorptiometry (DEXA) images of control (top) and STAT (bottom) mice (fat is colorized in light grey).
Figure 3B:
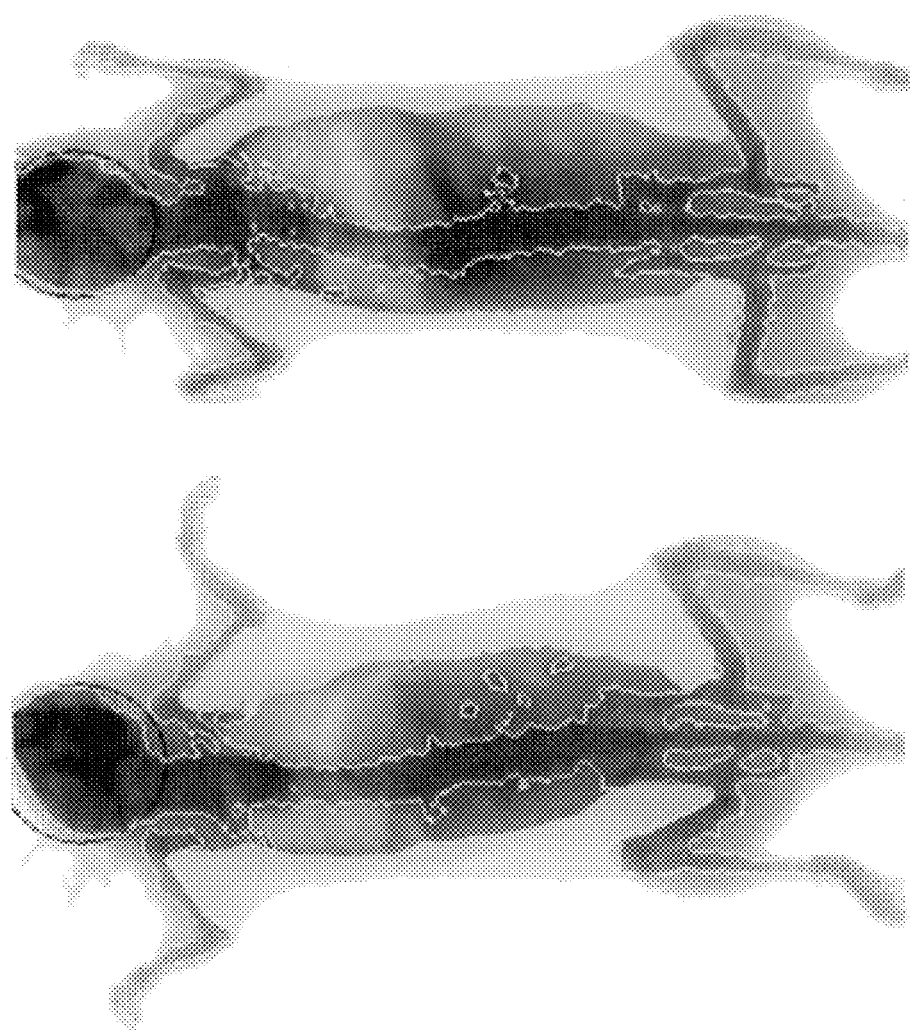
Figure 4:
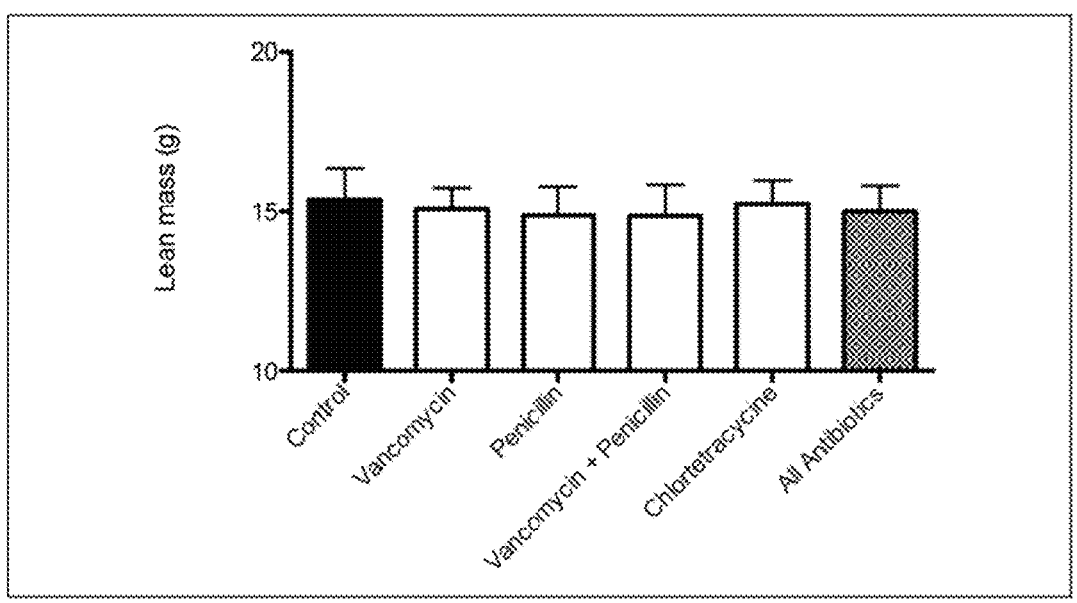
FIG. 4 shows a comparison of lean mass between sub-therapeutic antibiotic treated (STAT) and control mice at the time of sacrifice (day 63).
Figure 5:
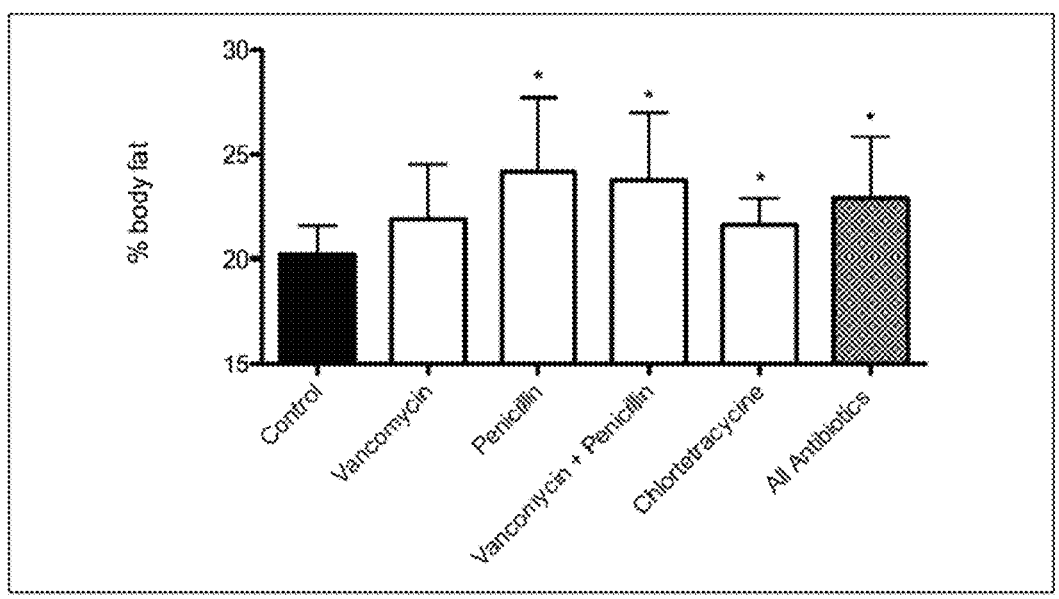
FIG. 5 shows a comparison of percent body fat between sub-therapeutic antibiotic treated (STAT) and control mice at the time of sacrifice (day 63).

FIGS. 3A-B show (A) a comparison of fat mass between STAT and control mice at the time of sacrifice (day 63) and (B) DEXA images of control (top) and STAT (bottom) mice (fat is colorized in yellow). FIG. 4 shows a comparison of lean mass between STAT and control mice at the time of sacrifice (day 63). The results show that none of the values is significantly different from the control. FIG. 5 shows a comparison of % body fat between STAT and control mice at the time of sacrifice (day 63). The results show that STAT mice had a 13.5% increase in their normalized % body fat compared to controls.

At 6 to 9 weeks, consistent and statistically significant increases in both normalized mean fat mass (FIG. 3A) and % body fat (FIG. 5) were observed in STAT mice as compared to controls. Compared with controls, STAT mice had 14.1±2.5% more fat mass than controls (range: 8.1±3.4% [chlortetracycline] to 22.9±8.1% [penicillin]; *p<0.05 by Mann-Whitney U-test). These results provide evidence that STAT mice have altered metabolism, leading to greater deposition of adipose tissue. These results are consistent with the effects observed in antibiotic-treated farm animals (Jukes, Bioscience 1972; 22: 526-534; Butaye et al., Clin Microbiol Rev 2003; 16:175-88; Gaskins et al., Anim Biotechnol. 2002; 13:29-42).

7. Analysis of Hormonal Phenotypes

Figure 10:
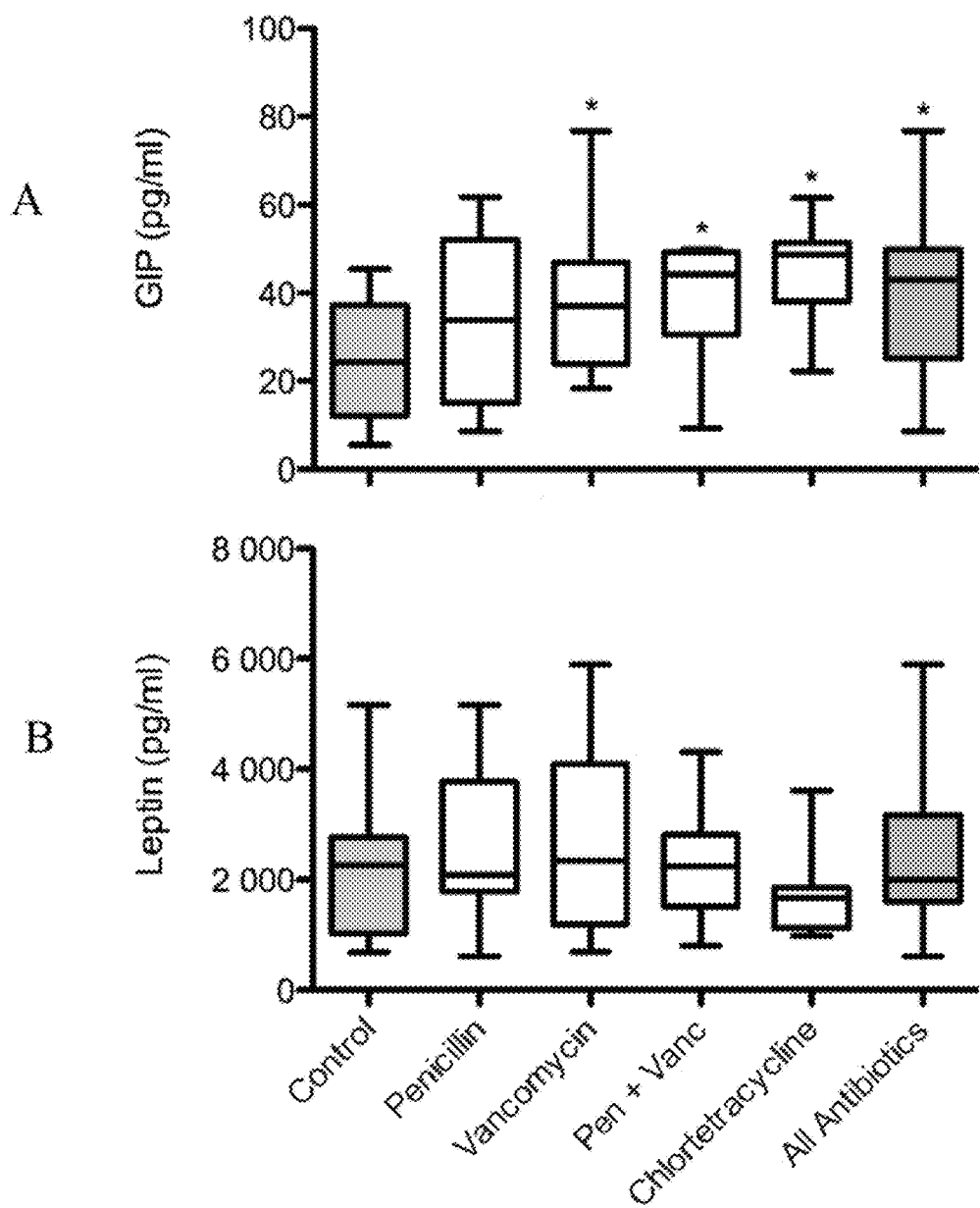
FIGS. 10A-B show comparison of two hormones related to energy homeostasis in sub-therapeutic antibiotic treated (STAT) and control mice. Levels of gastric inhibitory polypeptide (GIP) (A) and leptin (B) were measured by Luminex microsphere-based bioassay. *p<0.05 (Mann-Whitney U-test). Plots show Medians and IQR±2×SD.

Using Luminex microsphere-based bioassays (Luminex Corporation, Austin, Tex.) at sacrifice, serum levels of five hormones related to energy homeostasis were evaluated in STAT and control mice. Insulin, IGF-1, leptin; and ghrelin levels were not significantly different between STAT mice and controls. Since there was no difference in weight gain, the lack of difference in leptin was not surprising. However, gastric inhibitory polypeptide (GIP; also termed "glucose-dependent insulinotropic polypeptide") levels were significantly higher in STAT mice (39.1±2.5 pg/mL) than in controls (24.4±4.2 pg/mL) (a 59.5% increase; *p<0.05 by Mann-Whitney U-test) (FIGS. 10A-B). Since parallel significant effects were observed in three of the four independent treatment groups, this suggests that antibiotic exposure perturbs the homeostasis of GIP, which is a known incretin, produced by the intestinal epithelium (Hansotia and Drucker, Regul Pept 2005; 128:125-34). Thus, the knowledge of fasting GIP status could be used in conjunction with microbial genotype data as a diagnostic of predisposition to obesity. In addition, treatments that directly decrease GIP levels could be used to reduce adiposity. Indeed, recent animal studies have shown that blocking GIP receptor leads to less obesity and improved insulin sensitivity (McClean et al., Am J Physiol Endocrinol Metab 2007; 293(6):E1746-55).

8. DNA Extraction

Approximately 10 mg of fecal or cecal samples were suspended in a solution containing 500 μl of extraction buffer (200 mM Tris (pH 8.0), 200 mM NaCl, 20 mM EDTA), 210 μl of 20% SDS, 500 μl of a mixture of phenol:chloroform (pH 7.9, 24:24), and 500 μl of a slurry of 0.1 mm-diameter zirconia beads. Cells were lysed by mechanical disruption with a bead beater set on high for 2 min at room temperature, followed by extraction with phenol:chloroform (pH 7.9, 24:24), and precipitation with isopropanol. After the sample was suspended in 100 μl of TE buffer, the extraction products were further purified using a modified protocol from the ExtractMaster Fecal DNA extraction kit (Epicentre Technologies, Madison Wis.). Residual protein was precipitated using the Protein Precipitation reagent and inhibitors were removed through an Inhibitor Removal Resin spin column. The final product was suspended in 100 μl of TE buffer.

9. RAPD-PCR

Characterization of the microbial population in the fecal samples was performed using random amplified polymorphic DNA PCR(RAPD-PCR). Samples were screened using random primers 1254 CCGCAGCCAA (SEQ ID NO: 1), OPL-02 TGGGCGTCAA (SEQ ID NO: 2), or OPL-12 GGGCGGTACT (SEQ ID NO: 3). A reaction mixture of 50 μl was prepared containing 5 μl 10× buffer, 4 μl 10 mM dNTP, 1 μl RAPD primer, 0.25 μl Taq polymerase, 38.75 μl ddH$_2$O, and 1 μl template DNA. Amplification was performed in a thermal cycler with initial denaturation at 95° C. for 5 minutes, 40 cycles of denaturation at 94° C. for 1 minute, primer annealing at 34° C. (primer 1254, SEQ ID NO: 1), 42° C. (OPL-02, SEQ ID NO: 2), or 38° C. (OPL-12, SEQ ID NO: 3), extension at 72° C. for 2 minutes and a final extension at 72° C. for 5 minutes. Amplified products were separated in 1% agarose gels. The gels were stained with ethidium bromide and imaging was analyzed using imageJ. The results of the RAPD-PCR reactions are shown in FIGS. 6-8.

Figure 6:
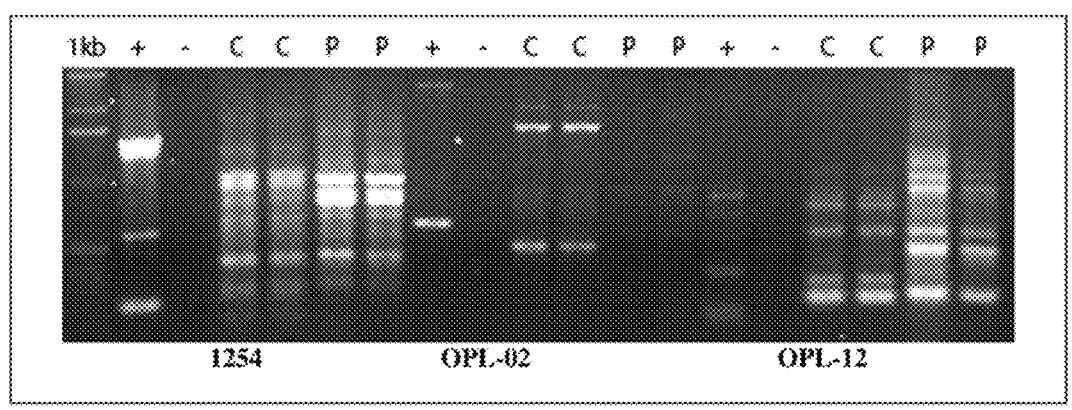
FIG. 6 shows a gel of RAPD-PCR analyses of fecal DNA for penicillin-exposed and control mice using three random primers.

FIG. 6 shows a gel of RAPD-PCR analyses using primers 1254 (SEQ ID NO: 1), OPL-02 (SEQ ID NO: 2), or OPL-12 (SEQ ID NO: 3) of DNA extracted from the cecal contents of two penicillin-exposed (P) and two control (C) mice. The positive control (+) was DNA from *P. acnes* strain VPI 0389. The negative control (−) was the RAPD-PCR cocktail with no DNA template added. The results show clear differences between the products in the penicillin-treated and the control mice with each of the three primers. These results provide evidence for change in the bacterial populations due to the antibiotic treatment that correlate with changes in body fat metabolism.

Figure 7:
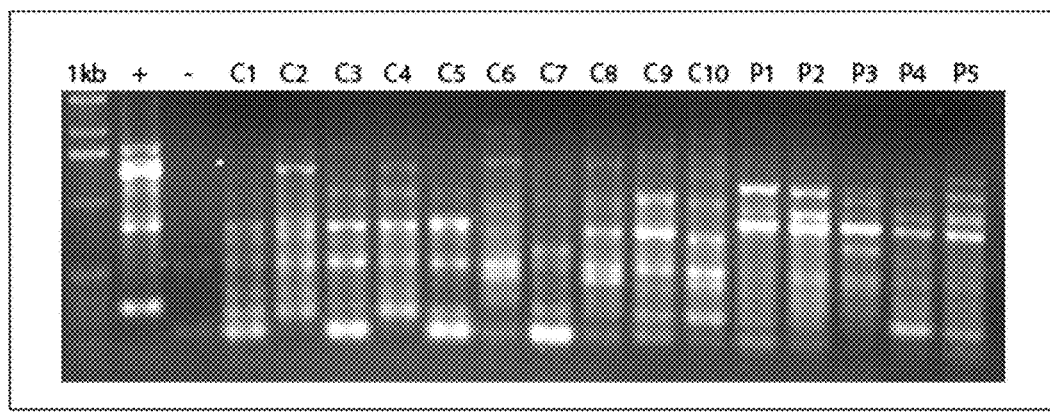
FIG. 7 shows a gel of RAPD-PCR analyses of fecal DNA for penicillin-exposed and control mice using random primer OPL-12.

FIG. 7 shows a gel of the RAPD-PCR analyses using random primer OPL-12 (SEQ ID NO: 3) of DNA extracted from the cecal contents of 10 control mice (C1-C10) and 5 penicillin-exposed mice (P1-P5). The positive control (+) was DNA from *P. acnes* strain VPI 0389. The negative control (−) was the RAPD-PCR cocktail with no DNA template added. The letters A, B, C over columns C10, P1, and P2, respectively, were analyzed be measuring luminescence (see FIGS. 9A-B). The results of this study with a larger group of mice confirm and extend the results from FIG. 6.

Figure 8:
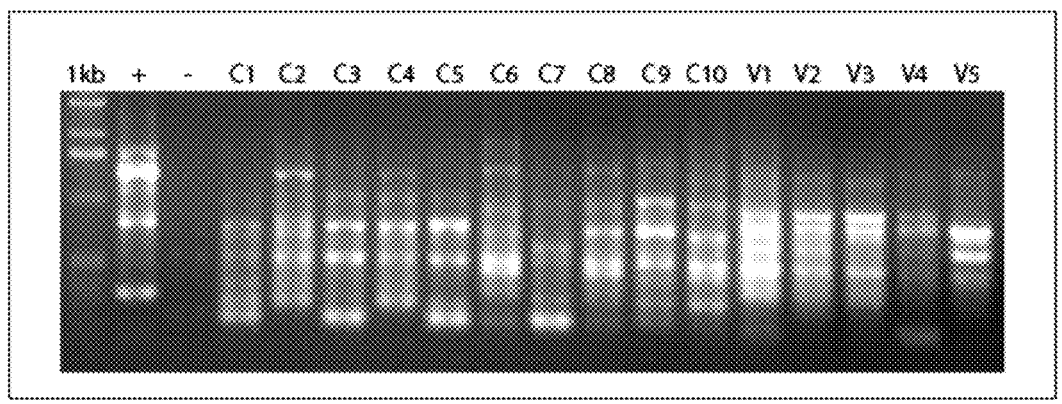
FIG. 8 shows a gel of RAPD-PCR analyses of fecal DNA for vancomycin-exposed and control mice using random primer OPL-12.

FIG. 8 shows a gel of the RAPD-PCR analyses using random primer OPL-12 (SEQ ID NO: 3) of DNA extracted from the cecal contents of 10 control mice (C1-C10) and 5 vancomycin-exposed mice (V1-V5). The positive control (+) was DNA from *P. acnes* strain VPI 0389. The negative control (−) was the RAPD-PCR cocktail with no DNA template added. The control samples were run in lanes marked "C" and exhibited common and unique bands, with several strong common bands. The test vancomycin exposed samples were run in lanes marked "V" and exhibited varying sets of bands. The results of this study using a different antibiotic (vancomycin) again confirm and extend the results from FIG. 6.

Figure 9:
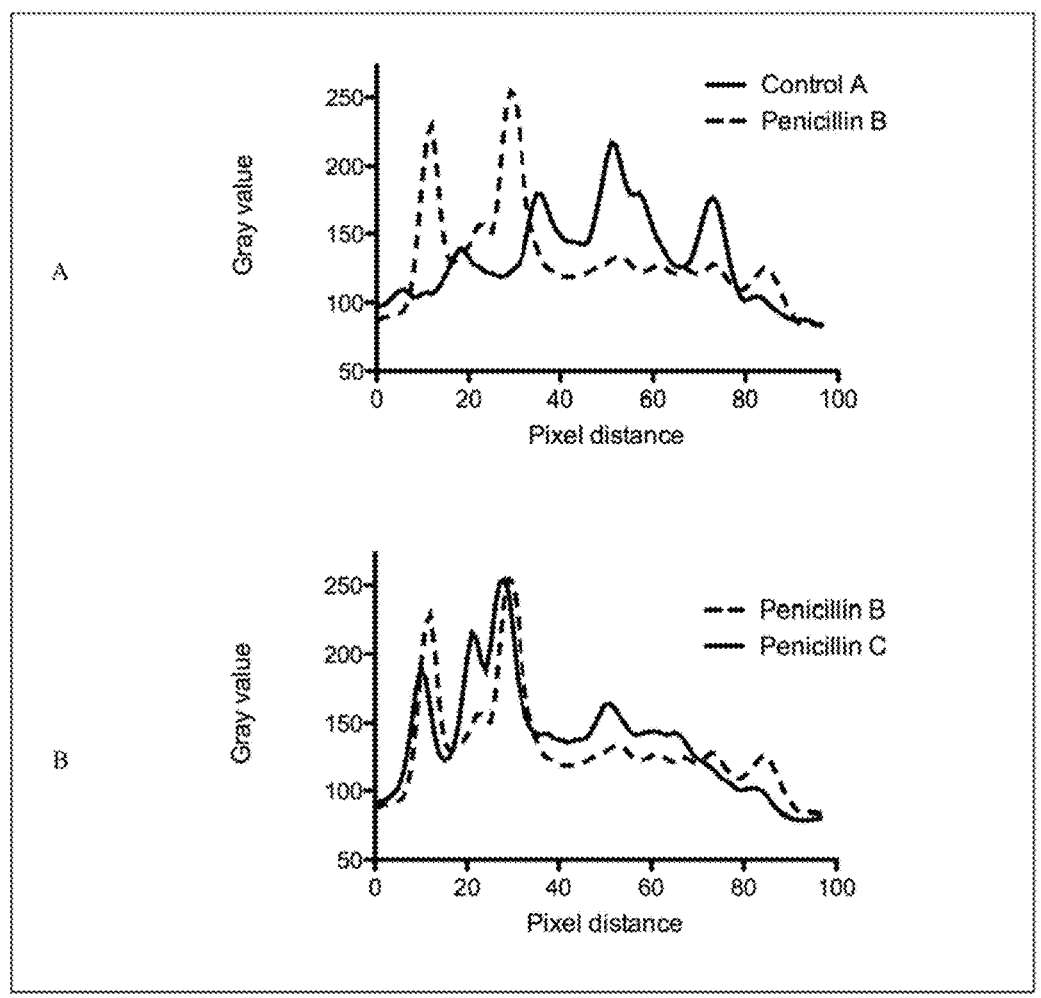
FIGS. 9A-B show a comparison of representative RAPD-PCR analyses using ImageJ profile plots of the agarose gels from FIG. 7.

FIGS. 9A-B show a comparison of Image) profile plots of representative RAPD-PCR agarose gel results. The lanes scanned are from the experiment shown in FIG. 7, using random primer OPL-12, and the sample lanes are marked by the letters A, B, or C. There are notable differences in the plots of the control and penicillin-exposed mice (FIG. 9A), whereas plots from two penicillin-exposed mice show similar profiles (FIG. 9B). These results provide consistent genomic patterns that aid in the resolution of the exact microbiome genotypes that are responsible for the change in body metabolism.

10. Identification of Bacteria Affected by Obesity-Inducing Antibiotic Treatment by 16S rRNA Analysis and Metagenome Analysis by High-Throughput Sequencing.

DNA extracted from cecal and fecal specimens was subjected to PCR using barcoded universal primers interrogating the V3 region of the 16S rRNA gene followed by 454 sequencing and taxonomic analysis.

Analysis of total microbial counts in STAT Mice. One of the possibilities for how low-dose antibiotics can lead to a change in metabolism is that they suppress total microbial levels. This possibility was addressed by examining total fecal eubacterial levels in penicillin-treated and control mice by a standardized quantitative PCR (qPCR) using primers ACTCCTACGGGAGGCAGCAG (SEQ ID NO: 4) and ATTACCGCGGCTGCTGG (SEQ ID NO: 5) directed to conserved 16S rRNA fragments. Total fungal levels were determined by qPCR using primers directed to the conserved ITS2 region in the fungal rrn operon ITS1F CTYGGTCATT-TAGAGGAAGTAA (SEQ ID NO: 6) and ITS2 RCTGCGT-TCTTCATCGWTG (SEQ ID NO: 7) and probe TCYG-TAGGTGAACCTGCRG (SEQ ID NO: 8). The results (FIG. 1) showed no significant difference between the control and penicillin-treated mice in number of copies of bacterial or fungal rrn elements. These data indicate that the differences in adiposity do not reflect total bacterial load, and suggest that composition differences are critical.

Figure 12:
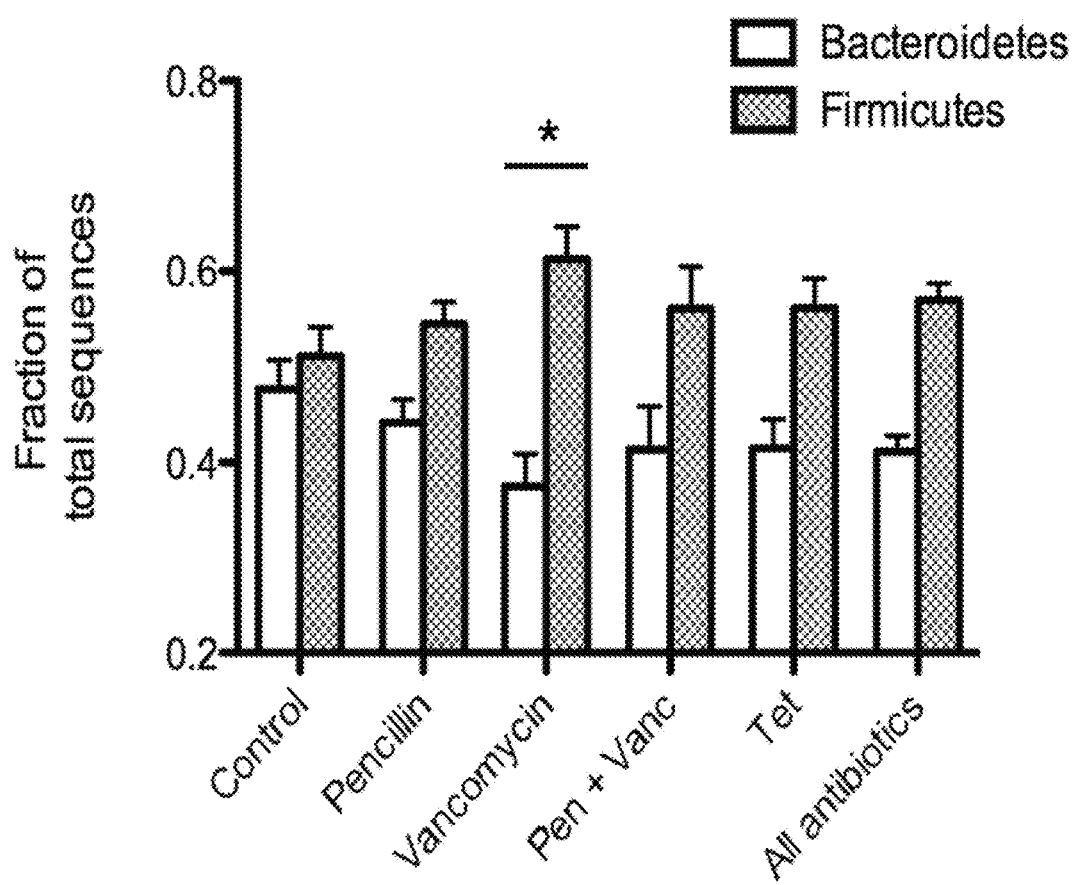
FIG. 12 shows proportion of Bacteroidetes and Firmicutes in the cecal microbiota of control and sub-therapeutic antibiotic treated (STAT) mice. Mean values±SEM are plotted. *p<0.05 (Mann-Whitney U-test).

Phylum-level analysis of bacterial populations in SCAT mice. In mammals, >90% of all colonic bacteria are in the phyla Firmicutes or Bacteroidetes (Ley et al., Nat Rev Microbiol 2008; 6:776-88). Mouse cecal contents were analyzed by 454 pryosequencing (Roche). Briefly, bacterial DNA was extracted from cecal contents and presence of amplifiable whole genomic bacterial DNA confirmed using standard PCR with the 8F/1510R primers targeting the 16S rRNA: 8F AGAGTTTGATYMTGGCTCAG (SEQ ID NO: 9) and 1510R TACGGYTACCTTGTTACGACTT (SEQ ID NO: 10). The samples then underwent 454 sequencing using barcoded primers designed to interrogate the 16S rRNA V3 region. For this experiment, the sequencing run produced 555,233 barcoded sequences with an average read length of 188±2.5 base pairs, an average read/barcode of 5784±676, and a read quality of 35. A total of >100 MB of data were generated. Order-level sequence data were summated to the phylum level and analyzed. As expected, the Bacteroidetes and Firmicutes constituted the overwhelming majority of sequences, accounting for 98.3% of the sequence data, with Firmicutes (F) slightly higher than Bacteroidetes (B), also as expected (FIG. 12). In the STAT mice, there was a trend in each group for increased Firmicutes and decreased B/F ratio compared to the controls, which was statistically significant ($p<0.05$ by Mann-Whitney U-test) in the vancomycin-exposed mice. This trend is similar to the relative changes in microbiome composition that have been reported in genetically obese ob/ob mice and obese humans (Ley et al., Proc. Natl. Acad. Sci. USA 2005; 102:11070-5; Ley et al., Nature 2006; 444:1022-3; Turnbaugh et al., Nature 2006; 444:1027-31; Turnbaugh et al., Cell Host Microbe 2008; 3:213-23; Turnbaugh et al., Nature 2009; 457:480-4). Inter-individual variation diminished the statistical significance of the differences between the groups in total, consistent with the recent data on the individual-specific effects of ciprofloxacin treatment (Dethlefsen et al., PLoS Biol 2008; 6:e280).

Figure 13:
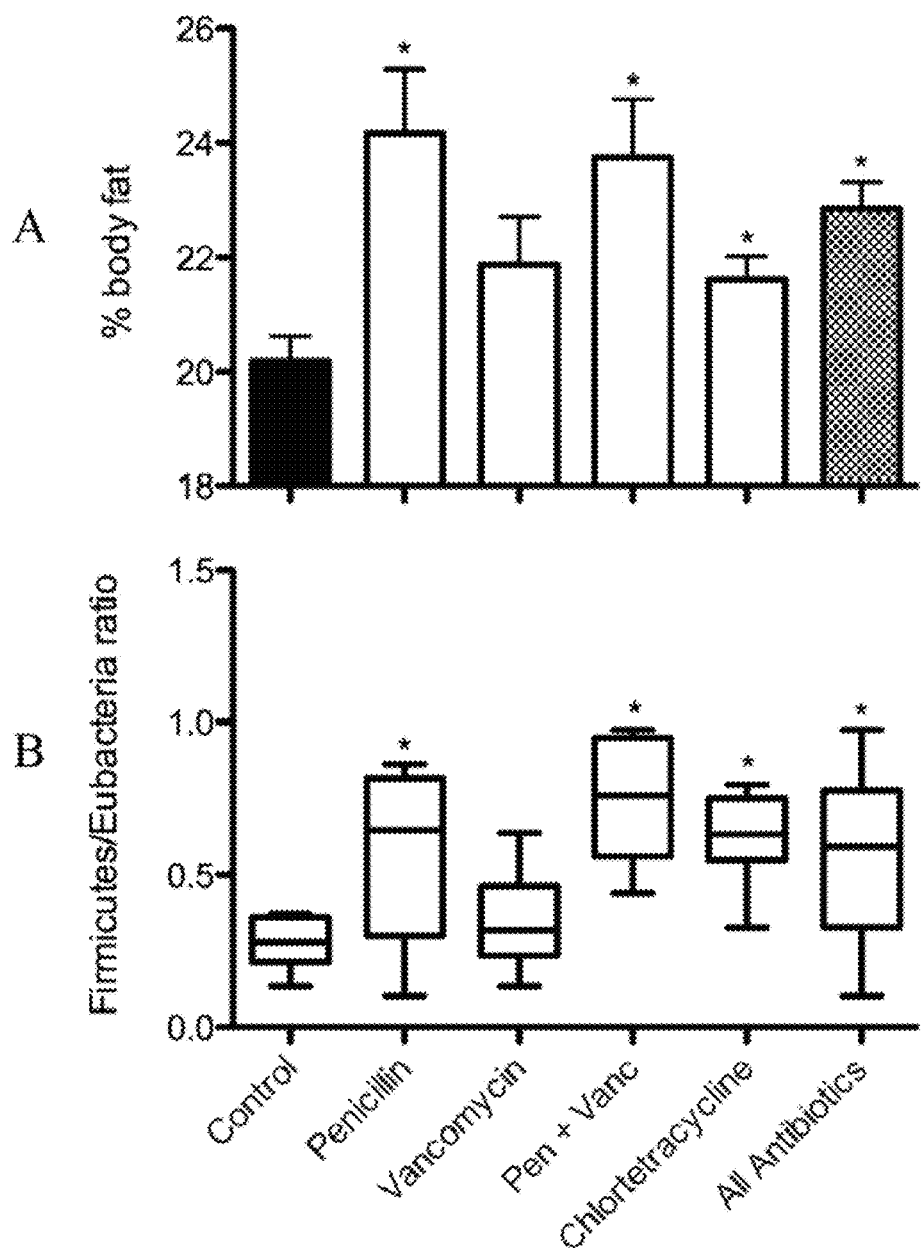
FIGS. 13A-B show that the % body fat measured by densitometry of the control and sub-therapeutic antibiotic treated (STAT) mice (A) correlates with the ratio of Firmicute/Eubacteria as determined at the family level by 454 sequencing (B).

In another analysis, the proportion of all of the Eubacteria detected that were represented by the Firmicutes was examined. As shown in FIGS. 13A-B, % body fat measured by densitometry of the control and STAT mice (A) correlates with the ratio of Firmicute/Eubacteria as determined at the family level by 454 sequencing (B). In total, the STAT mice had higher proportions (significant in 3 of the 4 antibiotic groups, and in total) of Firmicutes to the total populations, and the proportions observed correlated with the differences in % body fat. This is consistent with the data in obesity mouse models and in obese humans (Ley et al., Proc. Natl. Acad. Sci. USA 2005; 102:11070-5; Ley et al., Nature 2006; 444:1022-3; Turnbaugh et al., Nature 2006; 444:1027-31; Turnbaugh et al., Cell Host Microbe 2008; 3:213-23; Turnbaugh et al., Nature 2009; 457:480-4).

Figure 11:
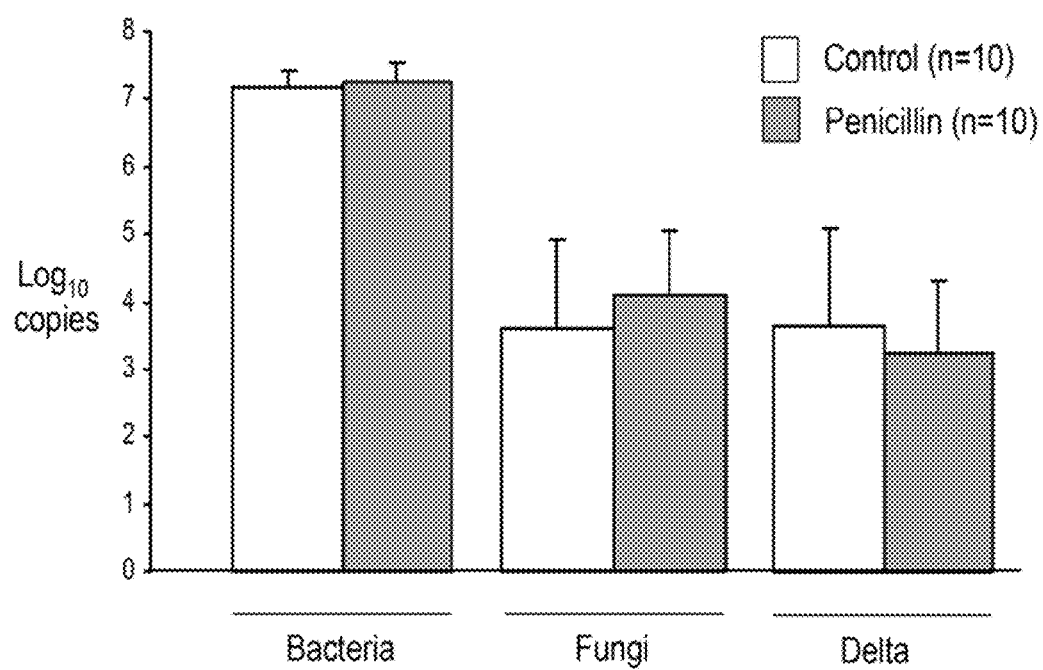
FIG. 11 shows comparison of the number of copies of microbial rRNA in fecal pellets from penicillin-treated and control mice.

Analysis of microbial taxonomic data in relation to adiposity. The above studies provide evidence that the STAT exposures do not substantially affect total numbers of bacteria and fungi in the intestinal contents (FIG. 11), but affect the proportions at high taxonomic levels (phylum) (FIG. 12). These data point to the utility of hierarchical clustering analysis at multiple taxonomic levels of complex population structures to identify genotypic relationships with specified host metabolic phenotypes.

qPCR of functional genes involved in colonic metabolism. Microbes can contribute to obesity through fermentation of non-digestible carbohydrates in the colon to short chain fatty acids, such as acetate, butyrate, and propionate (FIG. 14, taken from Pryde et. al., FEMS Microbiol Lett 2002; 217(2):133-139). See Bergman, Physiol Rev 1990; 70:567-90; Wong et al., J Clin Gastroenterol 2006; 40:235-43; Pryde et al., FEMS Microbiol Lett 2002; 217:133-9; Wolfe, Microbiol Mol Biol Rev 2005; 69:12-50. This process represents a 75% energy conversion to a product that is readily absorbed in the intestine, contributing 10% of host caloric intake. In human fecal samples, the proportion of acetate:propionate:butyrate is 60:20:20, with most absorbed in the colon. In the liver, acetate is a primary substrate for cholesterol synthesis, whereas propionate inhibits cholesterol synthesis (Wright et al., Proc Soc Exp Biol Med 1990; 195:26-9; Wolever et al., Am J Clin Nutr 1995; 61:1241-7). Butyrate is the preferred energy source for colonocytes. Changes in microbial composition and in the abundance of microbial genes should affect the pathways shown in FIG. 14, and therefore affect human physiology.

The present inventors have hypothesized that increased Butyryl-CoA: Acetate CoA-transferase or other functional short chain fatty acid production genes can be diagnostic for an intestinal microbiome that leads to increased adiposity. Furthermore, monitoring Butyryl-CoA: Acetate CoA-transferase levels can be used to assess the efficacy of novel prebiotics targeting colonic health and weight loss.

Figure 14:
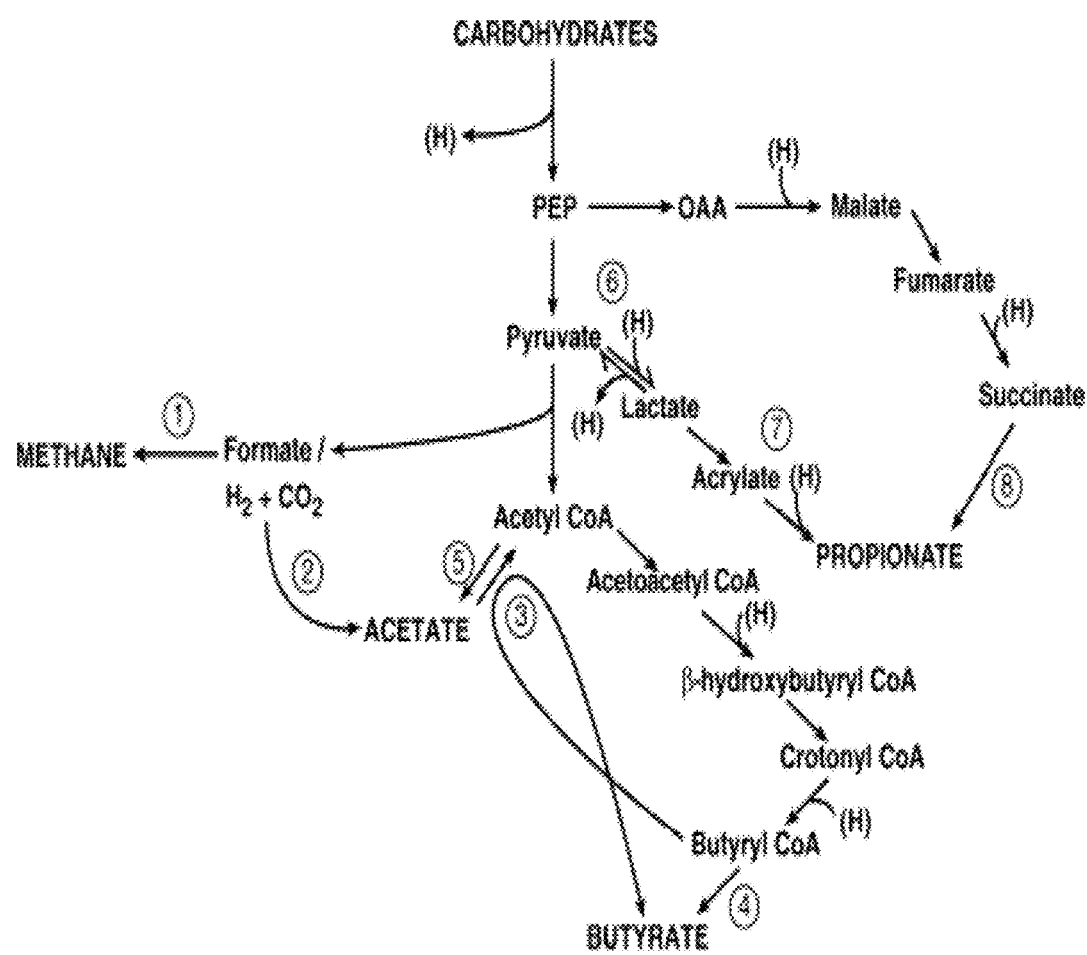
FIG. 14 is a schematic representation of pathways for carbohydrate fermentation in the large intestine (taken from Pryde et. al., FEMS Microbiol Lett 2002; 217(2):133-139). 1=Methanogenesis; 2=reductive acetogenesis; 3=butyryl CoA:acetate CoA transferase; 4=phosphotrans-butyrylase/butyrate kinase; 5=phosphotransacetylase/acetate kinase; 6=lactate dehydrogenase; 7=acrylate pathway, 8=succinate decarboxylation.
Figure 15:
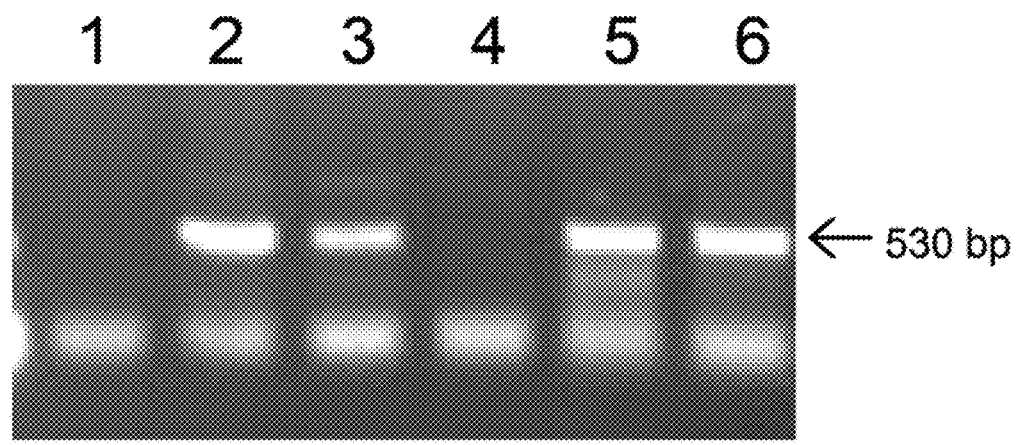
FIG. 15 shows a gel with the results of PCR analysis using degenerate primers for Butyryl-CoA transferase (BCoAT) gene. Lanes: 1, no template control; 2, genomic *E. limosum* DNA; 3, 1:10 dilution of genomic *E. limosum* DNA; 4, genomic *C. perfringens* DNA (negative control); 5, cecal sample from a control mouse; 6, cecal sample from a penicillin-treated mouse.
Figure 16:
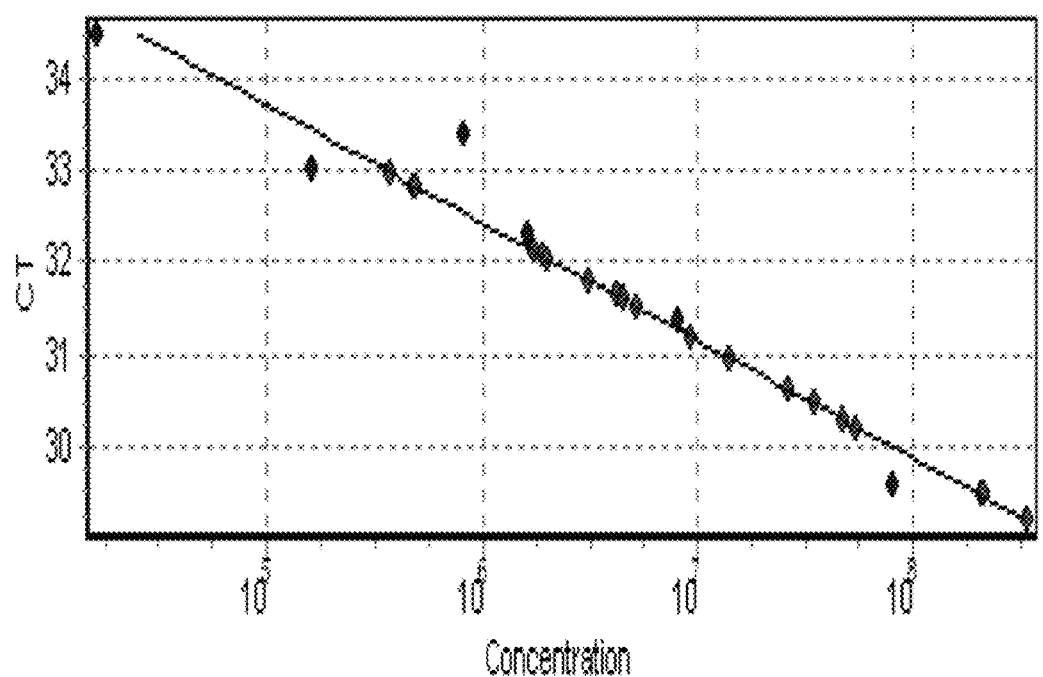
FIGS. 16A-D show the development of the Butyryl-CoA transferase (BCoAT) qPCR assay and its application to specimens from sub-therapeutic antibiotic treated (STAT) mice. Assay development involved *E. limosum* for standard curves (A), with clear quantitative amplification in qPCR (B). Application to penicillin-treated mice relative to controls (D) showed an increase parallel to the increase in % body fat (C).
Figure 16:
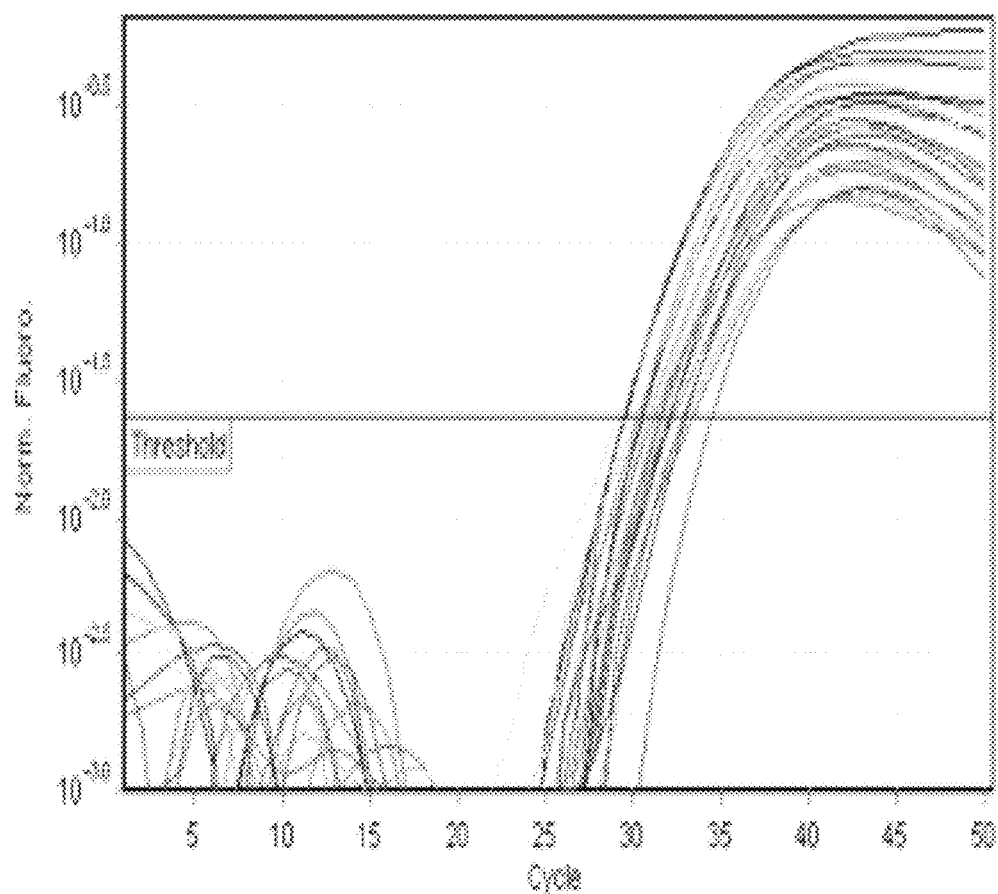

To test the effect of colonic microbiota on butyrate metabolism, a PCR assay was performed to detect genes encoding an enzyme, Butyryl CoA transferase (BCoAT), regardless of the taxonomic origin of the gene. The following primers were used: BCoATscrF GCIGAICATTTCAC-ITGGAAYWSITGGCAYATG (SEQ ID NO: 11) and BCoATscrR CCTGCCTTTGCAATRTCIACRAANGC (SEQ ID NO: 12). BCoAT plays a central role in butyrate metabolism, which is an important short-chain fatty acid (SCFA) in colonic metabolism and provides energy to colonocytes (FIG. 14). The assay worked well with both controls as well as cecal specimens, producing a heterogeneous population of BCoAT-encoding genes (FIG. 15; lanes 5 and 6 show the analysis of the cecal samples from a control mouse and penicillin-treated mouse, respectively). Development of a qPCR showed that it is possible to quantitate the heterogeneous populations of BCoAT genes (FIGS. 16A-D). Importantly, the STAT mice (penicillin-treated) show an increase in BCoAT densities compared to controls, paralleling the change in % body fat.

These data imply that changes in butyrate metabolism of colon microbiota lead to adiposity. Thus, inhibition of butyrate metabolism by affecting colon microbiota, for example, involving BCoAT, or other enzymatic pathways that affect butyrate homeostasis, could be used to either prevent or treat obesity. Similarly, presence of high BCoAT levels can be used in the diagnosis of the propensity to become obese.

EXAMPLE 2

Adjusting Cutaneous Microbiota to Treat MRSA Infection

This Example pertains to adjusting cutaneous microbiota. Adjusting cutaneous (i.e., skin) microbiota is helpful to prevent or treat such conditions as Methicillin-resistant *Staphylococcus aureus* (MRSA) infection. Opportunistic bacteria, such as methicillin-resistant *Staphylococcus aureus* (MRSA), are not only affecting patients who have been hospitalized, and/or recently received antibiotics, but also are causing infections in individuals who are perfectly healthy and who have not had any of the high-risk exposures. It is proposed that opportunistic bacteria, such as MRSA, can colonize and cause infections in such hosts due to the loss of indigenous microbiota due to prior antibiotic use, that could have been remote in time. An approach to this problem is to determine the nature of the missing bacteria and restore their populations by providing the bacteria, bacterial analogues, or prebiotics.

To determine the missing ("disappeared") biota, one would obtain skin and nasal swabs from MRSA affected persons and from healthy controls (as described by Gao et al., Proc. Natl. Acad. Sci. USA 2007, 104(8):2927-2932; and Paulino et al., J Clin Microbiol 2006, 44(8):2933-2941). DNA would be extracted from the swabs, as described by Gao et al. and Paulino et al. supra, and subjected to universal PCR for 16S rRNA genes to detect bacterial species present and for the intergenic spacer region (ITS) to detect fungi present. PCR products would be subjected to cloning, as described by Gao et al. and Paulino et al., or to high throughput sequencing (for example, using the Roche 454 sequencer). The species identities and abundances will be determined by comparison with the RDP database using Greengenes, as described by Gao et al. 2007, and Gao et al. (PLoS One, 2008, 3(7):e2719). By comparing affected and unaffected (contralateral side, e.g. comparing left and right arms) in the MRSA-colonized or affected person with the same sites in the healthy (control) person, we will be able to determine which species and which bacterial genes are over or under-represented in the MRSA+ person. Alternatively, the same analysis will be conducted comparing the nasal microbiome of MRSA-positive and MRSA-negative (control) persons. For example, if we found a consistent under-representation of particular coagulase-negative *Staphylococcus* species, non-Group A *Streptococcus* species (non-GAS), *Corynebacterium* species, or *Propionibacteria* species, in the MRSA-affected sites or persons compared to the healthy controls, we could enhance such populations by providing the organism or a bacterial analogue, or a prebiotic in a skin cream or ointment, or in an intranasal ointment. This formulation could be used to prevent the spread of MRSA among unaffected persons, as well as to maximize the likelihood of clearing MRSA in conjunction with direct anti-bacterial therapy.

Based on the species identification, it will be attempted to isolate the under-represented organism in pure culture, using selective microbiologic techniques (as described in the Manual of Clinical Microbiology, 8$^{th}$ edition). With the pure culture, the whole microbial genomic sequence will be determined in order to determine conserved metabolic genes across the affected populations. A strain that possesses and highly expresses the genes of interest will be included in the mixture of strains given to patients to restore their important metabolically active biota. Knowing the relevant species and genes also permits picking prebiotics that will stimulate the species and/or the specific metabolic pathways in the direction of health (control skin or nares). Such information also can be used to pick prebiotics that might inhibit deleterious pathways in the differentially-regulated organisms.

If the key organisms are not able to be cultured, the extracted DNA will be used to perform metagenomic analysis, comparing affected and control tissues. The candidate genes identified as over- or under-represented can be harnessed as discussed above. In this case, with the inability to grow the organism of interest, an approach based on prebiotics will be more important.

EXAMPLE 3

Adjusting Gastrointestinal Microbiota to Treat *C. difficile* Infection

Another opportunistic pathogen is *Clostridium difficile*, which has been spreading greatly in hospitalized patients, especially those receiving antibiotics (McDonald et al., N. Engl. J. Med. 2005). Therapeutic and prophylactic approaches already are in use with specific *Lactobacillus* and *Bifidobacterium* species (Fuller, J. Appl. Bacteriol. 1989, 66: 365-378). However, it is not clear that these populations have really been lost, are native to the adult human colon, and not surprisingly they have only minimal and not reproducible efficacy. Improved approaches are necessary.

An approach that parallels Example 2, as applied to fecal samples is proposed. The relevant comparison is between the fecal samples of patients with *C. difficile* infection and fecal samples of age- and gender-matched healthy controls. The above-described approach would be used (Example 2) to identify the consistently missing organisms in fecal samples, but also would include primers to detect the presence of Archaea. Because some of these *Clostridium, Streptococcus, Bacteroides*, and *Methanogenic* species may be difficult or impossible to culture, the prebiotic approaches, using substrates that favor their growth, may be most helpful. It is noted that certain *Bifidobacterium, Lactobacillus* and *E. coli* species have previously been utilized as probiotics (with modest efficiency) and are not included in the compositions of the present invention.

EXAMPLE 4

Administering *H. pylori* Strains to Treat Childhood-Onset Asthma and Related Disorders It has been previously demonstrated that *Helicobacter pylori* colonization is inversely associated with childhood asthma (Chen Y, Blaser M J., Journal of Infectious Diseases 2008; 198:553-60; Blaser M J, Chen Y, Reibman J. Gut 2008; 57:561-7). For prevention or treatment of childhood-onset asthma and related disorders, *H. pylori* strains will be restored to a child's stomach. An inventory of *H. pylori* strains will be available to physicians in a form that can be orally administered. Following administration of the selected *H. pylori* strain or strains, a culture of *Lactobacillus* species may be administered to suppress the *H. pylori* populations until more adult-like conditions develop in the stomach. The inventory of *H. pylori* strains will include those that are cag$^+$ (possessing a full functioning type IV secretion system that can inject the CagA protein and other *H. pylori* constituents into epithelial cell), and cag$^-$, as well as strains varying in VacA activity (of genotypes s1 or s2, m1 or m2, i1 or i2), and in expression of the type I or type II Lewis antigen pathways. The strain or stain combination (involving a total of 2 to 5 *H. pylori* strains) will depend on the genotype and phenotype of the child in relation to such issues as cytokine gene polymorphisms (e.g. IL-1 Beta receptor, TNF-α gene), Lewis blood group and secretor status, and HLA type.

EXAMPLE 5

Administering *H. pylori* Strains to Treat Obesity, Metabolic Syndrome, and/or Diabetes For prevention or treatment of obesity, metabolic syndrome, and/or diabetes, *H. pylori* strains will be restored to the patient's stomach. An inventory of *H. pylori* strains will be available to physicians in a form that can be orally administered. Following administration of the selected *H. pylori* strain or strains, a culture of *Lactobacillus* species may be administered to suppress the *H. pylori* populations until more adult-like conditions develop in the stomach. The inventory of *H. pylori* strains will include those that are cog-positive (possessing a full functioning type IV secretion system that can inject the CagA protein and other *H. pylori* constituents into epithelial cells), and cog-negative, as well as strains varying in VacA activity (of genotypes $s_1$ or $s_2$, $m_1$ or $m_2$, $i_1$ or $i_2$), and in expression of the type I or type II Lewis antigen pathways. The strain or strain combination (involving a total of 2 to 5 *H. pylori* strains) will depend on the genotype and phenotype of the patient in relation to such issues as cytokine gene polymorphisms (e.g. IL-1 Beta receptor, TNF-α gene), as well as polymorphisms involved in regulation of ghrelin, leptin, and insulin, as well as Lewis blood group and secretor status, and HLA type.

EXAMPLE 6

Administering *H. pylori* Strains to Treat Esophageal Diseases

For prevention or treatment of esophageal diseases, such as GERD or GEJAC, *H. pylori* strains will be restored to the patient's stomach. An inventory of. *H. pylori* strains will be available to physicians in a form that can be orally administered. Following administration of the selected *H. pylori* strain or strains, a culture of *Lactobacillus* species may be administered to suppress the *H. pylori* populations until more adult-like conditions develop in the stomach. The inventory of *H. pylori* strains will include those that are cog-positive (possessing a full functioning type IV secretion system that can inject the CagA protein and other *H. pylori* constituent's into epithelial cell), and cog-negative, as well as strains varying in VacA activity (of genotypes s1 or s2, m1 or m2, i1 or i2), and in expression of the type I or type II Lewis antigen pathways. The strain or stain combination (involving a total of 2 to 5 *H. pylori* strains) will depend on the genotype and phenotype of the patient in relation to such issues as cytokine gene polymorphisms (e.g. IL-1 Beta receptor, TNF-α gene, those involved in gastric acid secretion, including the regulation of gastrin, gastric somatostatin, gastric histamine-production, and otherwise affecting gastric acidity), Lewis blood group and secretor status, and HLA type. It is noted that the nature of the patient polymorphisms might affect the cog-positive to cag-negative ratio of the *H. pylori* to be administered.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for treating antibiotic-induced obesity by restoring one or more bacterial species depleted in a gastrointestinal microbiota of a mammal following an antibiotic treatment, wherein said mammal has developed or is at risk of developing obesity as a result of the depletion of said bacterial species in the gastrointestinal microbiota of said mammal, said method comprising:
   a) identifying one or more bacterial species which is statistically significantly diminished in a gastrointestinal microbiota sample obtained from the mammal following the antibiotic treatment as compared to a control gastrointestinal microbiota;
   b) culturing bacteria from the one or more bacterial species determined in step (a) to be statistically significantly diminished in said sample as compared to the control; and
   c) administering the cultured bacteria from step (b) to the mammal in an amount sufficient to increase the abundance of said bacteria in the gastrointestinal microbiota of said mammal and treat said antibiotic-induced obesity in said mammal.

2. The method of claim 1, wherein step (a) involves screening of bacterial 16S rRNA gene(s) and/or bacterial gene(s) involved in metabolism.

3. The method of claim 1, wherein step (a) involves PCR and/or high-throughput sequencing of bacterial 16S rRNA gene(s) and/or bacterial gene(s) involved in metabolism.

4. The method of claim 1, wherein the cultured bacteria are administered to the mammal together with a buffering agent selected from the group consisting of sodium bicarbonate, milk, yoghurt, and infant formula.

5. The method of claim 1, wherein the mammal is human.

6. The method of claim 1, wherein the cultured bacteria are administered orally.

7. The method of claims 1, wherein the mammal is a child.

8. The method of claim 1, wherein the control is gastrointestinal microbiota from one or more non-obese age- and gender-matched healthy mammals of the same species that were not subject to the same antibiotic treatment.

9. The method of claim 1, further comprising monitoring at least one parameter associated with obesity in said mammal.

10. The method of claim 1, wherein the one or more bacterial species are from phylum Bacteroidetes.

11. The method of claim 1, wherein the statistical significance is $p<0.05$ by Mann-Whitney U-test.

12. The method of claim 2, wherein the functional gene(s) involved in metabolism is gene(s) encoding Butyryl CoA transferase (BCoAT).

13. The method of claim 1, wherein step (a) comprises (i) determining the identity and amount(s) of one or more bacterial species present within said gastrointestinal microbiota sample, and (ii) comparing the amount(s) of the one or more bacterial species determined in step (a) to the amount(s) of the same bacterial species in the control.

* * * * *